United States Patent [19]

Deucher et al.

[11] Patent Number: 4,805,202
[45] Date of Patent: Feb. 14, 1989

[54] PORTABLE FIELD X-RAY DIAGNOSTIC SYSTEM

[75] Inventors: Joseph S. Deucher, Lyndhurst; Michael S. Kacsala, Maple Heights; Anthony D. Szpak, Parma, all of Ohio

[73] Assignee: Picker International, Inc., Cleveland, Ohio

[21] Appl. No.: 51,577

[22] Filed: May 18, 1987

Related U.S. Application Data

[63] Continuation-in-part of Ser. No. 877,885, Jun. 24, 1986, Pat. No. 4,727,564.

[51] Int. Cl.⁴ .............................................. A61B 6/04
[52] U.S. Cl. .................................. 378/209; 378/196; 378/195; 378/208; 269/322
[58] Field of Search ............... 378/193, 209, 195–198, 378/208; 269/322–325, 328

[56] References Cited

U.S. PATENT DOCUMENTS

| | | | |
|---|---|---|---|
| 2,668,912 | 5/1949 | Goldfield et al. | 378/196 |
| 2,754,426 | 11/1951 | Schiring et al. | 378/196 |
| 2,841,714 | 5/1953 | Vaughn | 378/196 |
| 4,589,126 | 5/1986 | Augustsson et al. | 378/209 |
| 4,613,122 | 9/1986 | Manabe | 378/209 |

Primary Examiner—Carolyn E. Fields
Assistant Examiner—Joseph A. Hynds
Attorney, Agent, or Firm—Watts, Hoffmann, Hoffmann & Heinke

[57] ABSTRACT

A compact, lightweight, portable, versatile and modular field x-ray system is disclosed. A base member is provided and supports an x-ray table. Two vertical masts are also coupled to the base, for movement alongside the table in a direction parallel to its longitudinal dimension. The masts move independently of one another but can also be linked together for movement in unison. A tube head is attached to one mast by articulated structure, including a series of offset arms, which affords the tube head 6 degrees of freedom of movement, both above and below the x-ray table. A spot film device is movable coupled to the second mast. The second mast and spot film device are manually removable from the remainder of the system for operation in radiographic only mode. When the masts are linked together, the tube head, because of the offsetting nature of the coupling arms, can be precisely vertically aligned with respect to the spot film device, and the entire assembly of masts, tube head and spot film device can be moved in unison for fluoroscopic panning.

23 Claims, 22 Drawing Sheets

Fig. 5
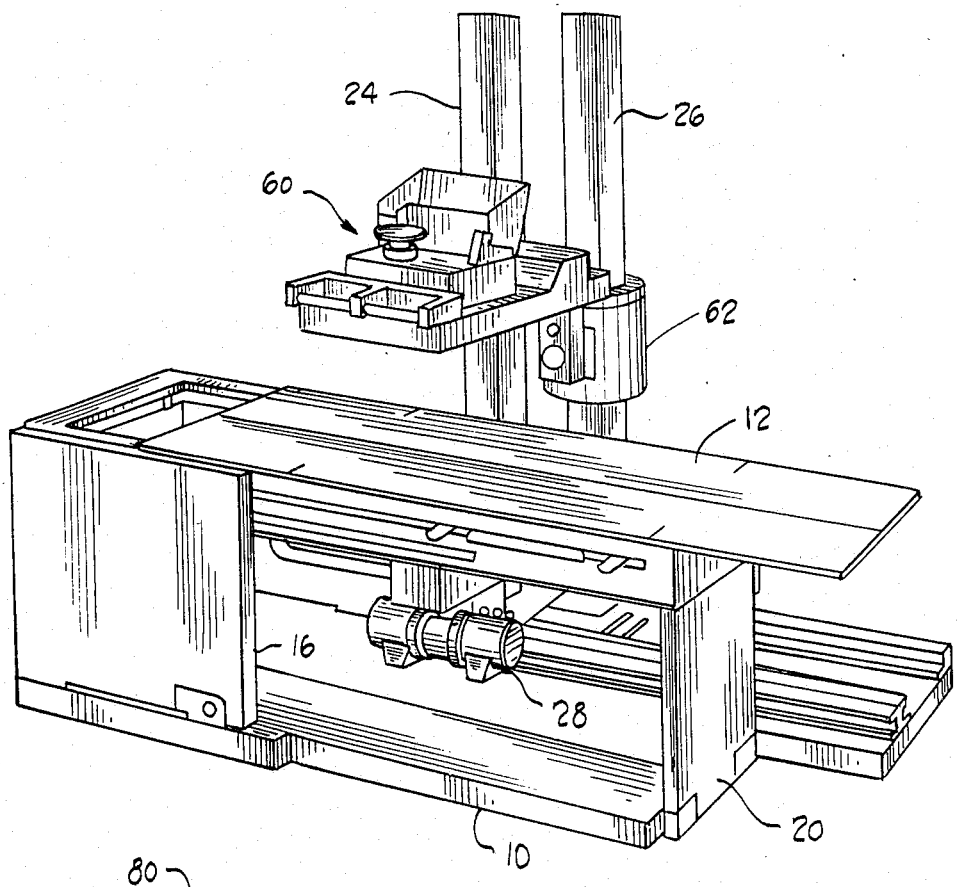
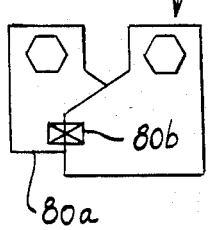
Fig. 5A

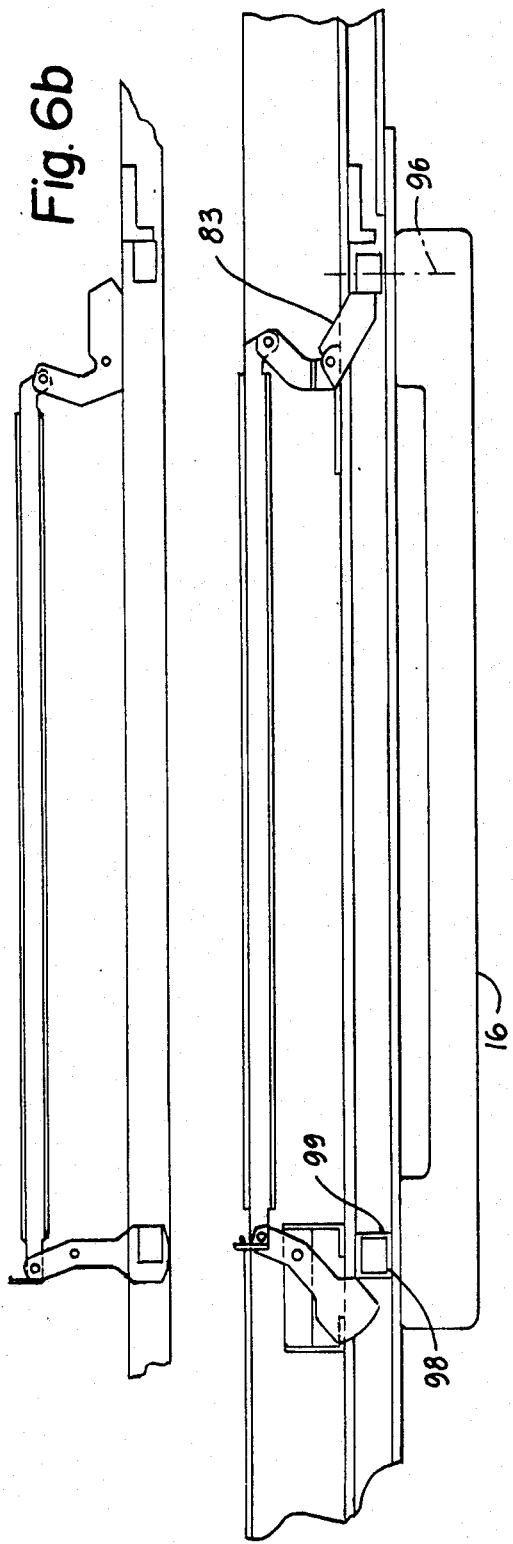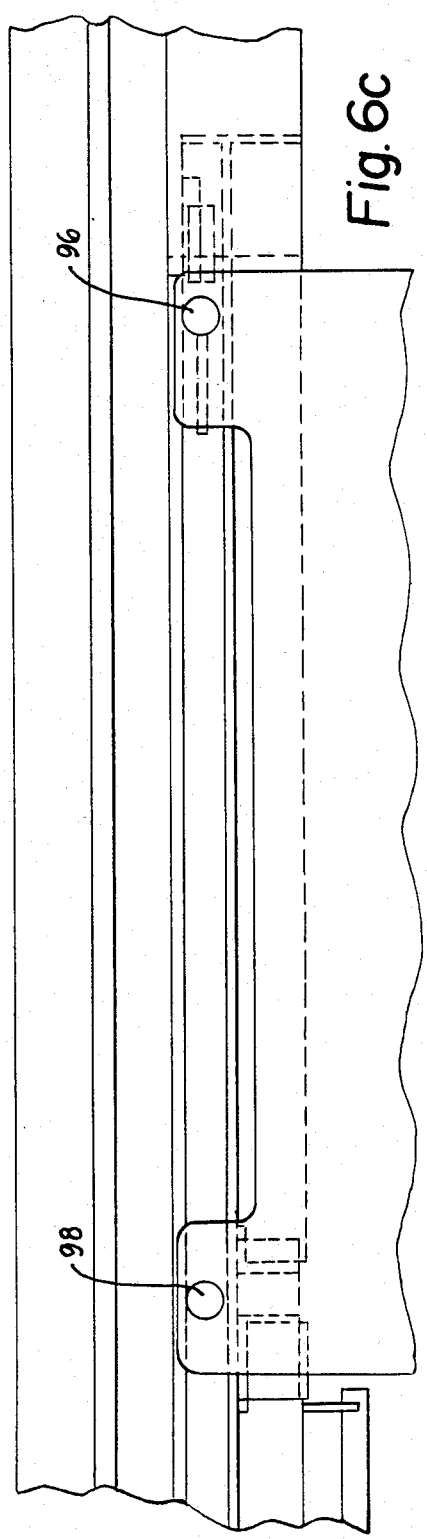

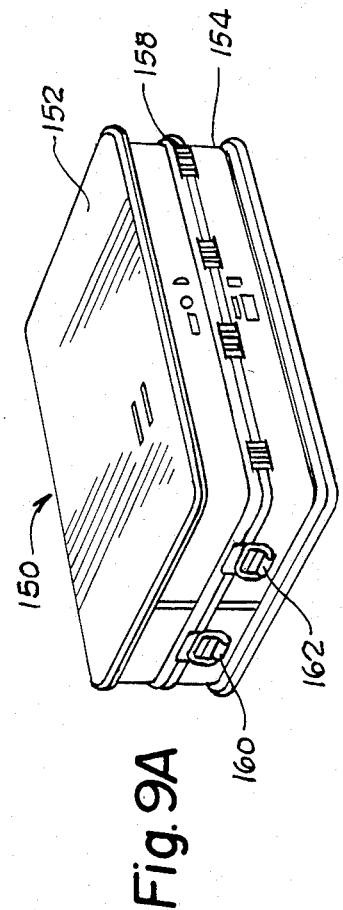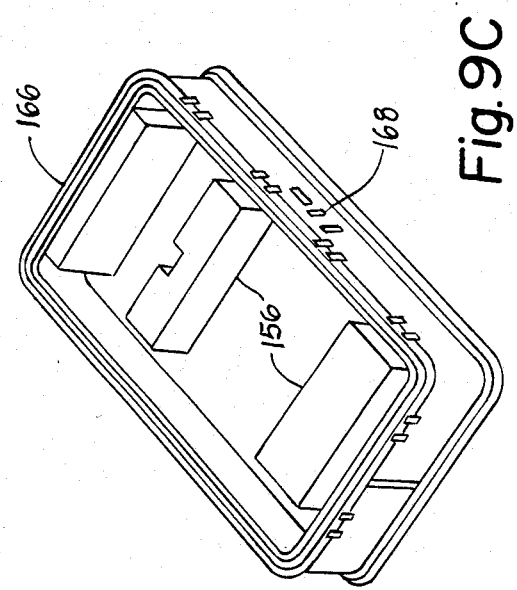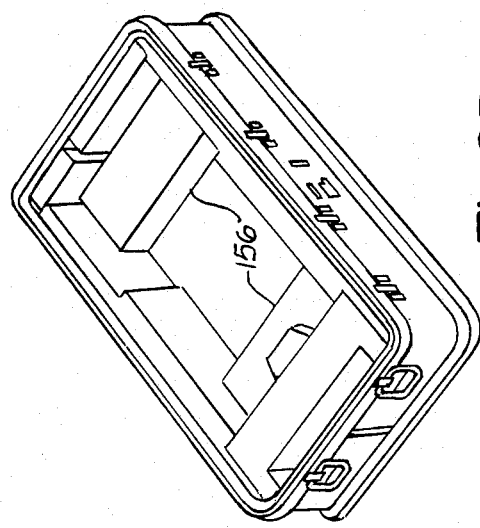

PORTABLE FIELD X-RAY DIAGNOSTIC SYSTEM

RELATED APPLICATION

This application is a continuation-in-part of co-pending application Ser. No. 877,885 filed June 24, 1986, now U.S. Pat. No. 4,727,564, entitled Portable Field X-Ray Diagnostic System.

TECHNICAL FIELD

This invention relates to the field of medical diagnostics, and more particularly to a lightweight, compact, portable and versatile combination radiographic/-fluoroscopic method and apparatus.

BACKGROUND ART

In a conventional radiography system, an x-ray source is caused to direct a divergent area beam of x-rays through a patient. A cassette containing an x-ray sensitive phosphor screen and film, sensitive to light and x-rays, is positioned in the x-ray path on the side of a patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

Many operating mode geometries are used in radiography and fluoroscopy.

In some applications, the patient reclines on an x-ray table having a top surface through which x-rays can pass with little attenuation. The source is located above the table and projects x-rays downwardly through the patient's body. The table is equipped with means, often called a "bucky", for accommodating and holding in place a radiographic film cassette just below the surface of the table.

In other applications, the source is located beneath the table top and projects x-rays upwardly through the table top and through the patient's body. A filmer assembly, having means to accommodate and support a radiographic film cassette, is located above the patient's body and aligned in the beam. These two applications are often referred to generally as "horizontal" radiography.

In another application, known as vertical radiography, the patient stands upright and a source is positioned in front of his body to propagate radiation through it along a geneally horizontal path. The radiographic film cassette or a spot filmer is supported behind the patient and is exposed by the x-rays.

In another type of radiography, known as "lateral", the patient reclines on the table, and the source is positioned generally beside the table to propagate its x-ray beam transverse to the longitudinal dimension of the table and through the patient's body. The radiographic cassette is appropriately supported on the opposite side of the table to receive the x-rays passing through the patient's body.

Still other radiogrpahic techniques are known as "oblique" work, in which the source is tilted or angled about one or more axes with respect to the table top to propagate x-rays through a patient lying upon the table. In one so-called oblique mode, the x-ray source is suspended over the table, and is rotated to an oblique angle, with respect to the table top, about an axis which is substantially horizontal and is perpendicular to the longitudinal dimension of the table.

Another radiographic technique defined here as "off table work" is typically performed using ceiling mounted x-ray systems or floor to ceiling mounted systems.

In fluoroscopy, a real time substantially continuous image, rather than a snapshot, of the patient's internal body structure is produced. The source directs x-rays through the patient's body, which are received by a fluoro device located on the opposite side of the patient. The fluoro device includes known means for producing a continuous image of the emergent pattern of x-rays transmitted by the patient's body. In fluoroscopy, the x-ray source is operated at a lower output level than in radiography. The output in fluoroscopy, however, rather than being a single pulse, is continuous.

Known types of fluoro devices employ a scintillation screen which responds to the incident pattern of x-rays to produce a directly visible image. Other types of fluoroscopic devices employ an image intensifier tube, which receives the x-ray pattern at a relatively large input face, and produces at an output face a corresponding image whose brightness is substantially enhanced with respect to the brightness of a simple scintillation screen. Where an image tube is used, the output is often viewed by a television camera and displayed on a monitor.

In fluoroscopy, mode geometries include those discussed above in connection with radiography, except for lateral, oblique and off-table work.

It can be seen from the foregoing discussion that, in order to accomplish all the various modes of radiography and fluoroscopy, the source and detector, be it radiographic film, a filmer assembly, or a fluoro device, must be positionable in a large multiplicity of locations with respect to the x-ray table and to the patient's body. This situation is complicated where a system is needed having the capability of practicing imaging in both radiographic and fluoroscopic modes, because of the necessity to support and position not only the radiation source, but also a radiographic film cassette, a filmer assembly, a fluoro device, and the patient.

Prior art x-ray systems either do not have the capability and versatility for performing operations in all the modes discussed above, or they are quite complex, bulky, and heavy, and require a permanent or fixed installation, such as including supporting walls and ceilings. Such systems also require large floor area to achieve such versatility.

One type of prior art system employs an x-ray source mounted only for location under the x-ray table in conjunction with a fluoro device and a filmer mounted on the table. Such devices obviously suffer from the disadvantage that they cannot be adapted to operate to position the source both above and below the table.

Other systems attempt to deal with the disadvantages of such systems by employing two sources, a first located above the table, a second located beneath it. The first source, located above the table, is typically mounted on either a ceiling supported track, a wall mounted track, or other tower structure. In such instances, the second source, located below the table, is dedicated for undertable use exclusively, and the above-table source is dedicated for overtable work. Such systems cannot stand independently of the support means provided by a fixed wall or ceiling.

Most prior art systems provide at least some of the desired component movement by means of electromechanical servo systems driven by controllable electric motors. The requirement for these servo drives is a disadvantage where space, weight and reliability are considerations, or where electric power is not readily available.

While systems such as those described above have been found satisfactory for operation in permanent installations, such as in permanent doctors' offices and large hospitals, these systems are inordinately complex and bulky for convenient use in portable applications. Such portable applications can include portable x-ray equipment for transport to a scene of traumatic injury, such as for use in conjunction with domestic trauma treatment centers, and in transportable military hospitals and first aid stations.

In such applications, it is particularly desireable that all equipment be as simple and reliable as possible, since repair capability may be inaccessible in the field. The equipment should be able to withstand repeated assembly and knockdown for transport. It must be capable of being knocked down, preferably without tools, into relatively small components which can be carried by humans without the aid of mechanical lifting and transport equipment, such as where it would be desireable to load an x-ray system in pieces into a vehicle for quick transport to and reassembly at a site of need.

Needless to say, x-ray equipment designed for portable application must be sufficiently rugged to resist damage or maladjustment resulting from vibration and other shock which normally occurs during transport of field equipment.

Another problem inherent in portable x-ray equipment is that, often, the equipment is used where electric power is in limited supply and form. It is sometimes a problem to find sufficient electric power, or the needed frequency, phase and/or voltage, to actuate relatively heavy electromechanical components such as motors and other servo equipment used to drive prior art type radiographic equipment.

The requirements of radiographic equipment used for initial evaluation of extensive traumatic injury often differ somewhat from the requirements for radiographic equipment used in permanent installations. Often, in portable units such as military field hospitals, sometimes called "MASH", the most important requirement for a radiographic system is to be able to reliably scan large areas of the human body very quickly, convert rapidly from one operating mode to another, and to rapidly produce images of reasonable quality illustrating gross traumatic injury caused by shrapnel, bullets and the like. It is also important to be able to perform a variety of radiographic and fluoroscopic procedures with little or no patient movement.

One previous military system was constructed in modular manner to break down into subassemblies which could be individually loaded into reusable containers for transport. This system, dating back to pre-World War II, was known as the "50/90" system, manufactured by Picker Corporation, of Cleveland, Ohio, U.S.A. Though the 50/90 system was satisfactory for some uses, it had several disadvantages. It had very limited provision for multiangle oblique radiographic operation. It had no spot filmer capability. Its fluoro was done with only a phosphor screen. In vertical radiography, the bucky could not be employed.

Previous commercial systems, sometimes referred to as portable, are extensions of previously made commercial products. Such systems are generally not free-standing, but require the attachment to a floor, a wall or a ceiling. As such, they cannot be used in places such as tent shelters. These systems are typically not particularly light in weight, since they are merely modifications of systems designed for non-portable use, such as in a hospital.

The support structures of the modified commercial systems were in many cases made of steel, and not suitable for field use by the military, because they were too heavy, or bulky and required floor, wall or ceiling anchor points.

Some previous specially designed military systems were designed to be portable and free-standing. Their support structures were generally of an open frame concept, made up of a multiple of conventional struts, bars, beams and trusses. Such members were joined to form a structural frame on which the various components of the system can be mounted.

The support structures of previously specially designed military systems have a number of disadvantages as well. Such structures are comprised of a number of separate members which do not have an obviously apparent assembly sequence, and are easily misplaced or lost. Such systems often used threaded connections, which may jam or cross thread. Previous military systems were designed such that operating personnel were impeded by the presence of significant structure obstructions in gaining access to both sides of the patient. This resulted in numerous trip points.

Some of the previous systems do not have sufficient structural strength and rigidity to support a state-of-the-art radiographic or fluoroscopic system, where image quality is highly dependent on system rigidity and freedom from vibration.

Additionally, such systems did not provide a surface for the patient to stand on when the table top is in the vertical position. Placement of carriage means for a mast supporting a radiographic or fluoroscopic head is such that the track means was close to ground level and subject to contamination by dirt, etc. Longitudinal tracks which guide the imaging system had to be tediously aligned during installation.

The great weight of the previous systems rendered their disassembly difficult for deployment.

It is an object of this invention to provide a lightweight, rugged, compact, versatile, reliable, simple, easily disassembled radiographic/fluoroscopic system capable of executing a large variety of radiographic and fluoroscopic operational modes, and without the need for the application of electromechanical power to move system components.

DISCLOSURE OF INVENTION

The disadvantages of the prior art are reduced or eliminated by the use of a compact, lightweight, simple, versatile and portable x-ray system for examining patients. Such a system includes a base and an x-ray table top defining a longitudinal dimension. Means is provided for supporting the x-ray table top above the base. The system includes first and second masts coupled to the base. An x-ray source is provided, along with means for coupling the source to the first mast. A fluoro device and/or a spot filmer assembly is coupled to the second mast.

The base and table supports for the system of this invention comprise mechanical structure that supports the table and mast assemblies of the fluoroscopic and radiographic (R/F) system of the present invention. The system is easily deployable in the field for examination of trauma patients.

The embodiments of the present invention include means for positioning, supporting and leveling of the X-ray table top, of the mast assemblies, of the X-ray source and of the imaging devices used. More specifically, leveling means is provided for the base, so that uniform leveling of the system can be accomplished irrespective of undulations or roughness of the ground or other surface on which the system is deployed.

A foldable, segmented base unit of the present invention acts as a deck, to provide safe and secure footing for patient and operating personnel alike. The base is low in profile.

The structure of the present invention is designed to be free-standing, foldable for compact transport, and capable of being deployed on uneven terrain. No tools are required to deploy the structure.

The use of composite honeycomb materials has resulted in a structure that is both rigid and light in weight. The design of the structure is such that deployment is simple, intuitive, and straightforward.

No known previous method or apparatus employs a foldable, rigid, flat, low profile base plate upon which the components of an X-ray and/or fluoroscopic system can be mounted.

In accordance with a more specific embodiment, the x-ray source is coupled to the mast by an articulated structure which supports the source for movement in 6 degrees of freedom.

More specifically, the articulated means includes a collar member mounted on the first mast, by way of vertical carriage member, for vertical motion up and down the first mast and additionally for rotative motion about a center line axis defined by the first mast. A first arm extends outwardly from the collar member. A second arm is mounted for pivotal movement with respect to the first arm about a substantially vertical axis. The second arm defines an axis generally extending along its longitudinal dimension Additional means is provided for coupling the x-ray source to the end of the second arm to facilitate the following movement of the source: rotative movement about an axis parallel to the second arm axis; rotative movement about an axis substantially horizontal and orthogonal to the second arm axis, and rotative movement about a vertical axis substantially orthogonal to the second arm axis.

One or both of the masts is coupled to the base by means which affords translational movement of the vertical masts along a horizontal path which is substantially parallel to the longitudinal dimension defined by the table top when the top is horizontal.

Additionally, when the articulated arm twin mast system is coupled with a table support and pivoting system whose pivot axis is located near the middle of the table length, the result is a substantial shortening of the required longitudinal length of the overall system while allowing clinically preferred relative orientations of patient, x-ray source table top and film. By contrast, in the above referenced 50/90 system, the X-ray tube could not be brought to the right of the table when vertically oriented without substantial system alteration. The center table pivot of the present invention, combined with the other movements provided, allow achievement, within a short longitudinal length, of a 40 inch S.I.D. in vertical radiographic mode as well as an acceptable S.I.D. in vertical fluoro mode. This nonobvious combination of a multiplicity of possible geometries forms a unique highly versatile compact system.

It can be seen from the above description that this system possesses unusual versatility in terms of being able to position the x-ray source above or below the table top, with a range of motion provided by the unique configuration of the slides, pivots, and geometry of the entire system. This system is capable of conversion among horizontal table fluoro, horizontal table radiographic, horizontal table lateral, and horizontal table oblique, including Townes, modes of operation, all without removing the patient from the table. This is a very important feature in trauma centers.

Additional flexibility is provided by means which is employed to mount a filmer assembly and/or fluoro device on the second mast. A carriage with a collar member mounted on the second mast affords vertical movement up and down the mast and rotational capability for orbiting about an axis defined by the second mast. Additional means is provided for pivoting the fluoro device/filmer assembly for rotative motion about a substantially horizontal axis which is perpendicular to the axis of the second mast.

In instances in which both masts are translatable along one or more horizontal paths parallel to the table top longitudinal dimension, means is provided for selectively linking the masts together for movement in unison along their respective path or paths. Such a capability is useful in instances in which the system is operating in a fluoroscopic mode, and it is desired to move, or "pan" the fluoro system relatively over various portions of the patient's body, while maintaining source to film alignment.

There is a minimum center-to-center spacing between the two movable masts, since they cannot both occupy the same space. The offset nature of the tube mounting to the first mast, by way of the arm structure, enables the precise vertical alignment of the x-ray source, mounted on the first mast, with the fluoro device, mounted on the second mast, notwithstanding that the masts themselves cannot be moved to the same longitudinal location with respect to the table top.

Additional flexibility is provided by means for mounting the table for various movements. The table is mounted for translational movement, when horizontal, in directions both parallel and perpendicular to its longitudinal dimension. Additionally, the table is mounted to switch between horizontal and vertical modes by translate and pivot apparatus for affording rotative movement of the table about a horizontal axis near the table center and perpendicular to its longitudinal axis. The table must be translated before being tilted, causing it to end up, after rotation in the middle of the base.

Importantly, the unique combination of offset in the x-ray tube support arm which is designed to permit movement of the tube offset either to the left or right of its support mast combined with a table tilt pivot position located in the central region (rather than at the end) of the table top results in a system where the effective movement of the x-ray tube is very extensive without the necessity for employing a long longitudinal track system. This permits achievement of a 40 inch S.I.D. in vertical radiographic work, as well as vertical fluoroscopic work with adequate S.I.D. while still maintaining a short overall system length.

The unique configuration of twin mast and offset tube support arm and centrally positioned table also permits the achievement of a system that is extremely well suited to conversion to a radiographic only system by simply removing the fluoroscopic device, spotfilmer and its associated vertical support mast and longitudinal carriage. What remains is a highly flexible compact radiographic system having capability to do radiographic work in lateral, overtable and oblique Townes modes with the table top horizontal, with the cassette carrying device located behind the patient and under PBC control. It also has the capability to do vertical table radiographic procedures in both normal and oblique directions with the cassette carrying device located behind the patient and under PBL control.

To accomplish the total versatility of this sytem, the current state of the prior art typically utilizes an auxiliary ceiling, mounted, or floor to ceiling track mounted, x-ray source in addition to a table with x-ray source mounted below it.

The system also incorporates hand operable locking and braking means for fixing, when desired, the relative orientations of the various components among one another. Some brakes and locks are normally electrically actuated, but can be manually overridden. No lead counterweighting is used in the system. No elements are provided whose sole function is counterweighting. Due to the light weight and simplicity of the system, no means is required for providing mechanical advantage for executing operator induced component movement. Rather, all movement can be accomplished by direct application of manual applications of force by an operator on the components whose movement is desired.

The offset in the x-ray tube support arm is uniquely configured to also place the tube in line with the spot filmer when performing horizontal fluoroscopic procedures.

In accordance with additional specific embodiments of the present invention, a unique configuration is achieved, including a flat platform base, an "H"-configured left end table support and a right end table support consisting of a flat panel with an integral, pivotable gate or support wing. The right end support can be laid flat during vertical table positioning, to form a ramp giving access to the flat base platform.

According to another specific embodiment, the structure of the present invention employs hinges and quick-release fasteners resulting in a structure which is both rigid and yet can readily be broken down for deployment.

The use of composite sandwich panels to support a radiographic or radiographic/fluoroscopic X-ray system enhances both the strength and lightness of the system. For example, the base assembly panels can have an aluminum, or other durable type of skin, and a core of aluminum, honeycomb, foam, or balsa wood. A unique hinge system design, consisting of a special hinge, compression stop plates, and hinge latches or fasteners, is also included.

This invention includes means to make a light weight, rigid platform which is foldable, highly rigid, can be leveled when placed on uneven terrain, and can serve as an excellent foundation to support X-ray equipment which must operate with a high degree of mechanical stability to achieve good X-ray image resolution.

In accordance with a further aspect, the invention achieves a foldable platform which can be precambered, as provided by the adjustable compression stops, to approximately compensate for the weight of the payload and of the panels to which the hinges are respectively attached.

According to another aspect of the invention, the system employs structural members which are held together by manually actuable quick fasten and release fastening devices to attach the system components to the base structure.

An interlock is provided, wherein the X-ray table top cannot be pivoted from vertical to horizontal unless the right end table support is erect and locked on its vertical, table-supporting position.

Other aspects of the present invention will be appreciated from a reading of the following detailed description, and from the drawings, in which:

BRIEF DESCRIPTION OF DRAWINGS

FIG. 5 is an isometric view depicting the system of FIGS. 1 and 2 deployed in a horizontal table fluoroscopic mode configuration;

FIG. 5A is a plan view illustrating details of a portion of the system illustrated in FIGS. 5 and 2;

FIGS. 9A-9C are isometric drawings illustrating a manner of knocked down and storage for transport of a system in accordance with a system of the present invention;

FIGS. 19 and 20A illustrate, respectively, the base assembly of FIG. 14 in a folded configuration, and a detail of FIG. 20;

BEST MODE FOR CARRYING OUT THE INVENTION

Figure 1:
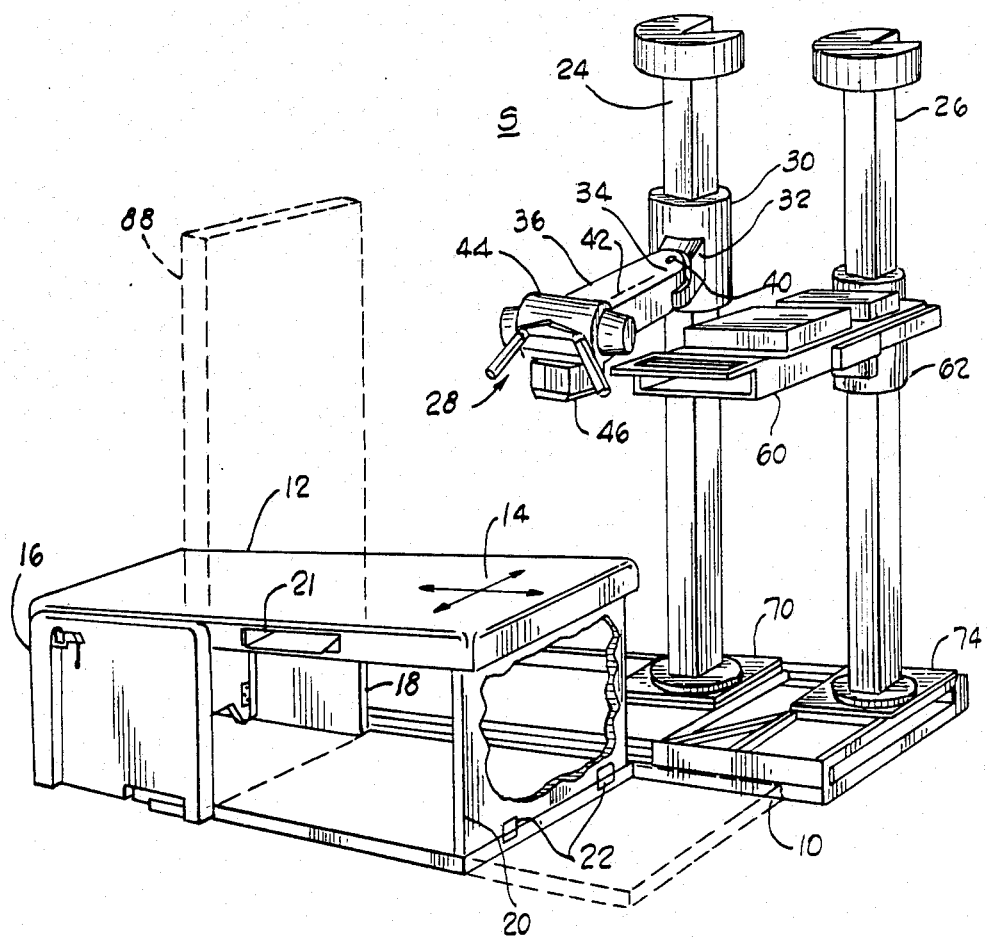
FIG. 1 is a an isometric drawing of a system embodying the present invention.
Figure 2:
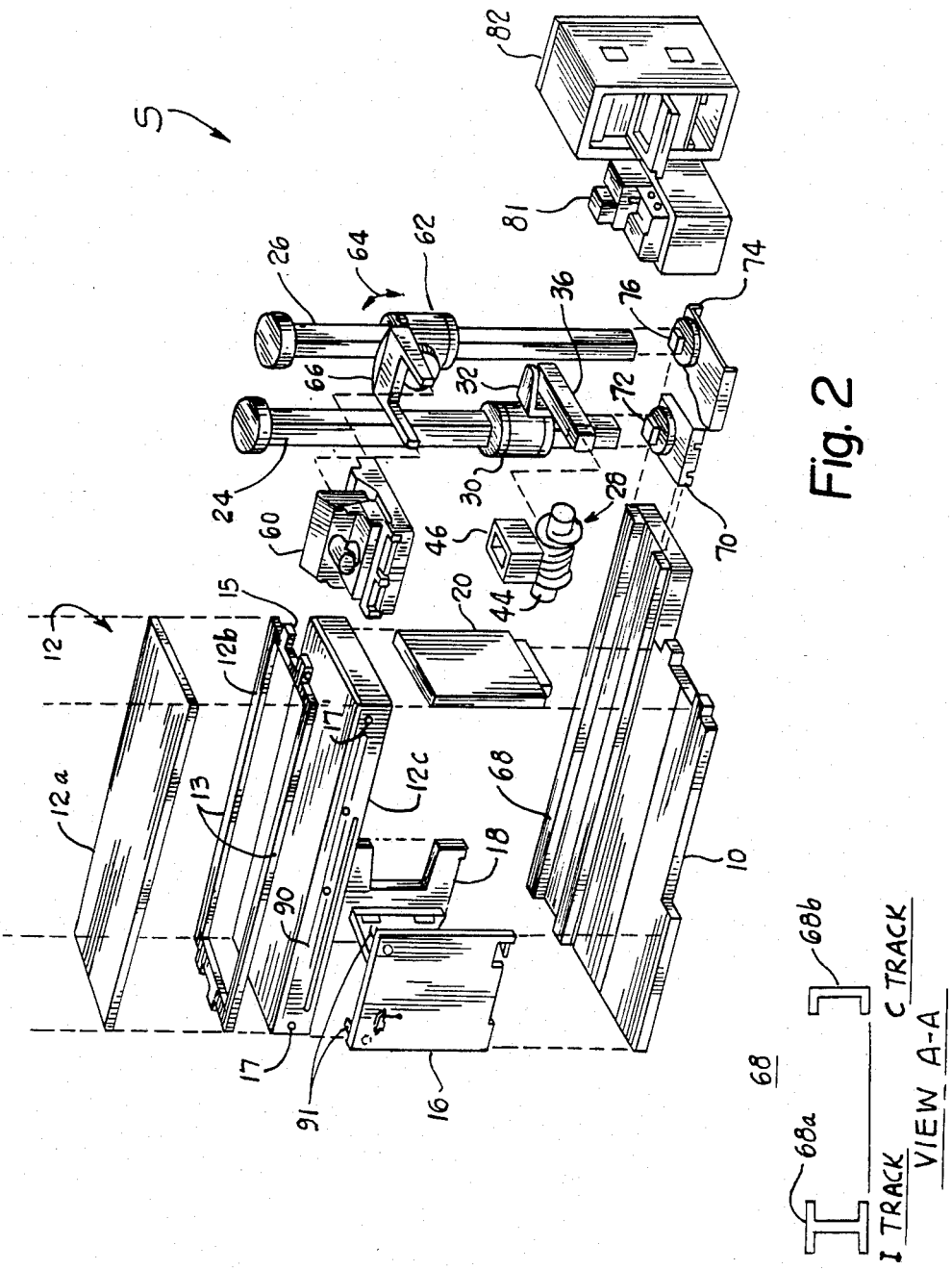
FIG. 2 is an exploded overall view of a system embodying the present invention.

FIGS. 1 and 2 illustrate in overall fashion an embodiment of a system S for carrying out the present invention. The system includes a base 10 which accommodates the mounting thereon of the other components of the system, and defines generally a small "footprint" or area occupied by the system S. The base 10 is made of an aluminum honeycomb material. The base 10 comprises several segments which are hinged together for folding into a more compact configuration for transport.

The base and table support structures described in this disclosure have numerous advantages over the prior art.

The use of composite panels yields a structure which is light in weight, compact, rugged, rigid and has high strength.

The base design has a low profile, is easily cleaned, provides good operator access to the rear of the table, and is relatively free of trip points.

A specially designed hinge connecting the base panels yields an assembly which has a low profile, as indicated above, and is precambered upwardly to be flat under load, thus providing an excellent platform on which to mount the associated mast track assemblies and table supports.

The design and construction of the various component assemblies is such that the method of deployment is obvious, intuitive, and requires no tools or loose parts. During deployment, the mechanical coupling of the table assembly, a table vertical latch, and a base mounted tilt interlock mechanism is accomplished automatically.

Both the base and associated structure for supporting the table are stable and free-standing.

An x-ray table assembly 12 is shown whose function is to support a patient during x-ray examination. The table assembly includes a table top 12a, a subframe 12b, and a support tilt frame 12c, as shown in FIG. 2. The table top member 12a is elongated and defines a longitudinal dimension extending generally in the direction of one of the arrows 14 shown in FIG. 1.

The table top member 12a is an elongated portion of rigid material which is generally transmissive of x-rays. The table top member 12a is mounted for movement with respect to the subframe member 12b by longitudinal means of known roller bearing structure which rides in tracks 13 in the subframe member 12b.

The subframe member 12b is, in turn, movably mounted for transverse motion with respect to the support tilt frame 12c. A pair of bearing supports 15 are mounted on each end of the subframe member 12b. On one end, the bearing support members each define a hole having a horizontal axis perpendicular to the longitudinal axis of the table top member. The holes defined by one pair of bearing support blocks are coaxial and of the same size. The bearing support blocks accommodate in the holes a shaft (not shown), at one end of the subframe member which are attached at point 17' to the support tilt frame 12c. The shaft is also horizontally aligned perpendicular to the length of the table top. The other end utilizes cam follower type bearing members which ride in a C-shaped channel and are therefore tolerant of dimensional changes between the members 12b and 12c.

It can thus be seen that the table top member 12a is enabled to "float" in two directions of movement, defined by the arrows 14 in FIG. 1, i.e., longitudinally and transversely.

Figure 6A:
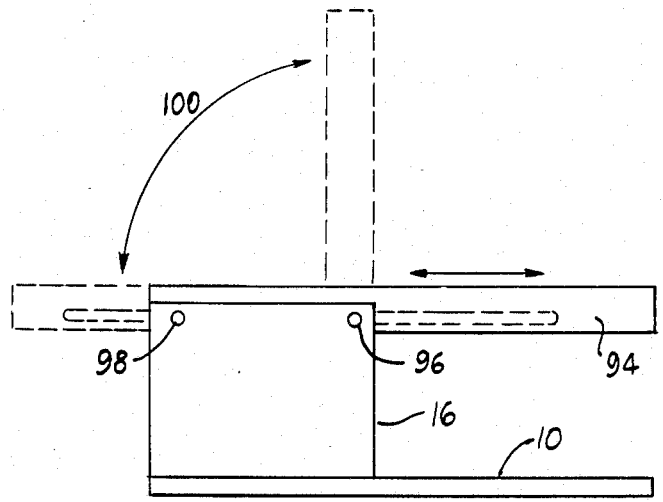
FIG. 6 is a front elevational view illustrating a portion of the system shown in FIGS. 1 and 2.

Additional provision is made for longitudinal movement of the entire table assembly. Slotted track structure 90 is provided in each side of the support tilt frame 12c. The track structure 90 is engaged in known fashion with roller bearings 91 in each of a pair of upright support panels 16, 18. In a manner described in more detail below, the sliding engagement of the support tilt frame 12c with the uprights 16, 18 permits the entire table assembly to be moved longitudinally. Table tilting is prevented unless the table assembly is moved a sufficient distance to the left as shown in FIGS. 2 and 6. When the table assembly is moved a sufficient distance to the left, the slot and track structure 90, and bearings 91, permits tilting rotation of the table top to a vertical position.

This selective tilting capability is enabled by known bearing capture and gate mechanism associated with the track structure 90, and bearing structural 91, which maintains the table assembly in a horizontal position until the table assembly is moved to a predetermined point on its longitudinal travel path, and the gate is actuated by an operator.

Referring to FIG. 1, the table assembly also incorporates a radiographic film cassette tray on its underside. The cassette tray 21 is adjustable in position longitudinally with respect to the table top member 12a and 12b.

Means is provided for supporting the table top member 12 above the base 10. The table top supporting means includes the pair of upright side panels 16, 18, and a right hand end panel 20. The right hand end panel 20 is hingedly coupled as at 22 to the base 10. This hinged coupling, as described in more detail below, enables the right hand end panel member 20, under appropriate circumstances, to be rotated downwardly in a clockwise direction as shown in FIG. 1 until it touches the surface upon which the base 10 rests. In this configuration, the right hand end panel 20 can thus be converted to form a ramp leading from the underlying surface to the upper surface of the base 10 to facilitate the movement of patients in wheel chairs or walking onto the base for examination, especially for vertical table work, and to permit positioning of the panel 20 in an out of the way location.

The right hand end member 20 is made of a polyester glass material with a foam core.

A first vertical mast 24, and a second vertical mast 26, are coupled to the base 10. Each mast defines a center line axis extending generally in a vertical direction.

Each of the masts 24, 26 comprises a portion of aluminum tubing having a generally polygonal cross-section.

An x-ray tube head 28 of known type is coupled to the first mast 24 by articulated coupling structure. The coupling structure includes a vertical carriage assembly 30 including a vertical carriage member 31 (see FIGS.

10A and 10B which is mounted for vertical movement up and down the first mast 24 and which forms a vertical carriage to which the remainder of an articulated x-ray tube head support structure is attached.

The vertical carriage assembly also comprises a collar member 33 which rotates clockwise and counterclockwise about the axis of the mast 24. Vertical movement of the carriage assembly is controlled by a brake and is restricted by vertical carriage stops at the top and bottom of the mast 24. Appropriate spring counterbalancing is applied to exert an upward force on the vertical carriage member which is approximately equal to the weight of the vertical carriage assembly, plus its payload. These braking and counterbalancing elements are of known variety and can easily be supplied by those of ordinary skill in the art.

The vertical carriage member 31 surrounds the mast and has rollers that engage and ride on the mast 24. The collar member 33 rotates about the vertical carriage member 31 to provide rotation about the first mast center line axis.

Extending outwardly from the collar member 33 is a first arm 32, which rotates and moves vertically in unison with the collar member 33.

A second arm 36 is mounted to the first arm 32 for pivotal motion about a vertical axis extending through a pivot point 34, displaced from the first mast center line axis.

The second arm 36 defines a longitudinal axis designated by reference character 42.

Figure 3:
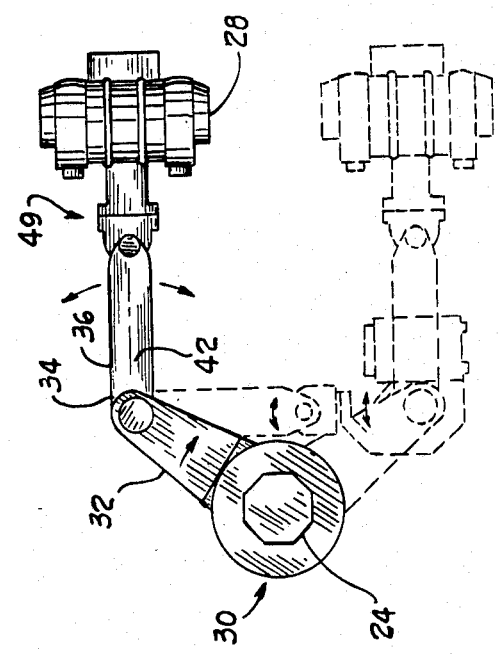
FIG. 3 is a detailed plan view illustrating a portion of the system of FIGS. 1 and 2.

FIG. 3 shows a plan view of the articulated arm structure described above for supporting the tube head 28 to the mast 24.

Figure 4:
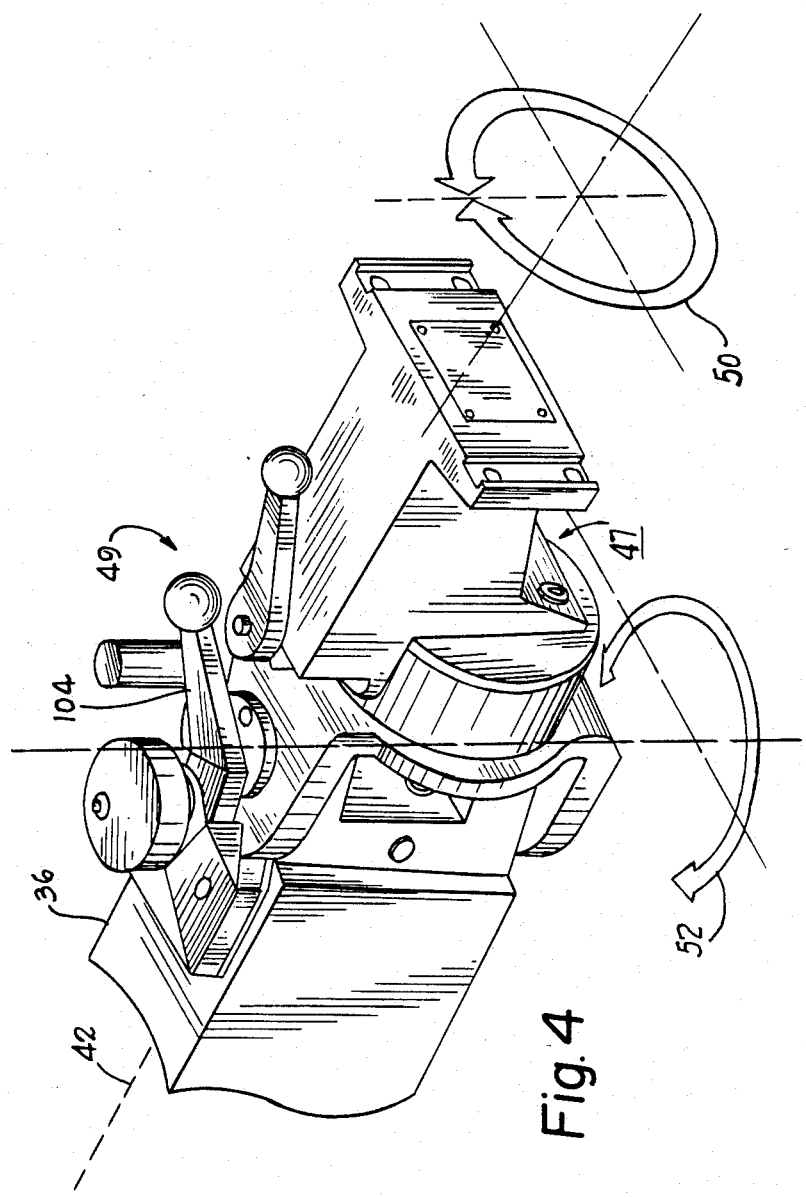
FIG. 4 is an isometric drawing illustrating in detail another portion of the system illustrated in FIGS. 1 and 2.

The x-ray tube head 28 is mounted on the outer end of the second arm 36. The x-ray tube head 28 comprises a known type of x-ray tube assembly 44, and a known type of collimator 46. The x-ray tube head is mounted for a variety of rotational motion about the end of the second arm 36, by apparatus as shown in FIG. 4.

First, apparatus 47 is provided for mounting the tube head for rotational movement about an axis substantially coincident with the second arm axis 42. Secondly, pivoting apparatus 49 supports the tube head for rotation about a vertical axis generally perpendicular to the second arm axis 42. See the curved arrows 50, 52. Detent apparatus can be provided in the pivot apparatus 47 and 49 to enable easy operator location of the "zero" angle positions for the tube head at which the tube is positioned to propagate radiation vertically down, and is aligned orthoganal to the second arm 36. Thirdly, the x-ray tube itself is supported on trunnions for tilting rotation about a horizontal axis perpendicular to the second arm axis 42.

It can be seen from the foregoing description of the articulated mounting of the tube on the first mast 24 that enormous flexibility is afforded regarding the location and orientation of the x-ray source 28. In fact, the x-ray source 28 can be positioned at virtually any location above or below the table, within the limits of the length of the mast 24 and of the arms. Within the limits of the system geometry, the tube can be tilted in virtually any direction with respect to the orientation of the table top 12. It can also be seen that the x-ray tube can be moved from a location under the table top 12a to a location over the table top 12a without the need for moving the table top 12a at all, and consequently without the need for disturbing a patient lying on the table.

A spot film device and/or a filmer assembly, generally designated at reference character 60, is movably coupled to the second mast 26. A portion of the coupling mechanism comprises a vertical carriage assembly 62. The vertical carriage assembly 62 comprises a vertical carriage member which moves up and down on the mast 26, and a collar member attached to the carriage member which rotates with respect to the carriage member and the mast. The construction of the vertical carriage assembly 62 is analogous to that described above in connection with the vertical carriage assembly 30. Rotation of its collar member is described by the arrows 64.

The spot film device and/or filmer assembly 60 is thus movable vertically with respect to the mast 26, and can orbit about the center line axis defined by the mast 26. In this way, when the spot film device 60 is not being used, it can be manually orbited away from the general vicinity of the x-ray table, to avoid interference with radiographic work. The spot film device is also spring counterbalanced to facilitate manual vertical adjustment.

Additionally, pivot apparatus is coupled between the spot filmer device and the collar member to provide manual rotation of the spot film device pivoting about a horizontal axis substantially intersecting the axis of the second mast 26, this horizontal axis also being defined by the vertical location of the carriage assembly 62. This permits rotation of the spot filmer for vertical table fluoroscopic work and for rotation to alternate park (storage) positions to the side, above or to the rear of the table. In the rear park position vertical patient access is non-obstructed by the filmer which is a distinct clinical advantage.

A spring counterbalance mechanism within this pivot allows rotation of the filmer about the mast with ease even though its center of gravity is substantially offset from the axis. This mechanism allows motion in both directions about the axis.

Reference to the exploded view of FIG. 2 illustrates in more detail the manner of coupling of the spot film device and fluoro imaging device to the collar member. This coupling is accomplished by way of a bracket 66 which defines a generally forked configuration into which the spot film device can be mounted in known fashion.

FIG. 2 (Section A—A) also illustrates in cross setion track structure for coupling the masts 24, 26 to the base 10. A track set 68 having I-shaped track structure 68 is defined by the base member 10, and extends along a straight line generally parallel to the longitudinal dimension defined by the x-ray table top member. A first carriage 70 is slidably engageable in the inner portion of the I-shaped track element 68a and to a C-shaped member 68b to afford low friction movement along the direction of the track. The carriage member 70 defines a recessed portion 72 into which the lower end of the mast 24 can be manually inserted. Appropriate hand actuable snap locks are provided to hold the mast in the recess 72. When the carriage member 70 is engaged in the track 68, and the mast 24 inserted in the receptacle portion 72, the entire mast 24, and all its payload, are manually and easily movable along the direction of the track 68.

A carriage member 74 is provided for similarly carrying the mast 26. The carriage member 74 is slidably engageable in the outer portion of the I-shaped track member 68a and in the C-shaped member 68b. The carriage member 74 defines a recessed portion 76 into which the lower end of the mast 26 can be inserted. Thus inserted, and with its carriage member mounted in the track 68, the second mast and its payload is also movable manually along the path defined by the track 68.

FIG. 2 illustrates, for purposes of completeness, a high voltage tank 81 and control console 82 for providing the electrical power for operating the spot film device, the tube head, and all electromechanical system components, in accordance with predetermined procedures. The high voltage tank 81 and control console 82 are of known type and can be provided by one of ordinary skill. The high voltage tank and control console are coupled to the tube head and spot film device and other components by appropriate cabling, which is not illustrated in an effort to avoid obfuscating the mechanical aspects of the present invention.

The respective movements of the masts 24, 26 can be independent of one another. In some operating modes, however, it is desirable for the masts 24, 26 to execute ganged movement, i.e., movement in unison. For this purpose, linking structure 80 (see FIG. 5A) is provided for decouplably linking together the carriages 70, 74, so that they and the masts 24, 26, move in unison, or separated, as desired.

The coupling structure comprises a solenoid actuated movable hook 80a on one carriage member, which is releasably engageable with a pin 80b on the other carriage member. The hook can be manually disengaged. The coupling is used when in fluoro mode, table horizontal, with variable S.I.D., and, in the table vertical fluoro mode, with fixed S.I.D.

It can be seen from FIGS. 1, 2 and 5 that, although the masts 24, 26 are generally movable independently of one another, the masts cannot obviously be precisely lined up with one another. Rather, there is a certain minimum center to center spacing between the masts.

It will further be seen that, due to the offsetting (displacement) of the x-ray tube head from the mast 24, because of the articulated arms 32, 36 coupling the tube head to the mast, the tube head can be extended to be precisely vertically aligned with the spot film device 60. This could not be achieved without the offsetting of the tube head from the mast 24.

This offset could optionally be achieved with the tube head being slidable along an arm, rather than by the pivot articulation described here.

When it is desired to execute a horizontal fluoroscopic technique, the tube head is manually moved by way of its articulated coupling structure and vertical carriage member, to a fixed height beneath the table. The tube head is oriented to direct radiation vertically upwardly through the table, and is precisely vertically aligned with the spot filmer 60, attached to the other mast 26, which is in this configuration above the table and above the patient's body. The fluoro device can be moved vertically while the tube remains vertically stationary to vary the S.I.D.

FIG. 5 illustrates the system of this invention operating in the above described vertically aligned horizontal fluoroscopic mode. In this configuration, the masts 24, 26 are linked together for movement in unison, and the tube head 26 is precisely vertically aligned with the spot film device 60. In this configuration, the entire assembly of masts 24, 26, tube head 28, and spot film device 60 can be moved in unison longitudinally over various portions of the patient's body, in an operation known as "panning". Also, the table top 12a can be moved in the directions of the arrows 14 in FIG. 1, to enhance panning.

Preferably, rough positioning for panning is done by moving the masts, and actual panning done by movement of the table top 12a in one or both directions horizontally.

FIG. 5A, mentioned above, illustrates in some detail a plan view of the mechanism for coupling together the carriage members 70, 74. Briefly stated, the mechanism 80 comprises a solenoid actuated movable hook member 80a, attached to one of the carriage members 70, 74 and a pin member 80b attached to the other carriage member. The hook and pin are aligned such that, when the carriage members 70, 74 are moved together, the hook will ride over and engage the pin, thus holding together the carriage members 70, 74 for movement in unison. When it is desired to decouple the carriage members, the solenoid is actuated to cause the hook to retract and disengage from the pin, upon which the carriage members 70, 74 can be manually separated. Alternately, the hook member can be moved to disengage from the pin by the manual application of force.

The table assembly, as noted above, is tiltable about a horizontal pivot axis near its center, relative to its length, the pivot axis being perpendicular to the longitudinal direction defined by the table top. FIG. 1 shows the table top tilted to a vertical position as indicated by the phantom at reference character 88. FIG. 2 illustrates the track structure 90 associated with the side panel members 16, 18, into which the support tilt frame 12c is mounted, in association with roller bearing structure, for longitudinal sliding movement.

FIG. 6 illustrates the sliding and pivoting capabilities of the table top 12a in more detail. The support tilt frame member 12c is mounted for translation and rotation relative to the side panels 16, 18, about a pivot axis 96. Roller bearing structure, such as at 98, mounts the support tilt frame for sliding motion with respect to the side panels 16, 18. In use, when it is desired to tilt the table from a horizontal to a vertical configuration, the table is first slid to the left as shown in FIG. 6, (in phantom). The left hand roller bearing is released from the track when a pawl 83 is properly retaining the right roller bearing 96. This automatically latches when the table has been moved sufficiently to the left. A clearance gate 99 allows vertical passage of the support tilt frame 12c past bearing 98. The table is then subsequently rotated in a clockwise direction about the pivot axis 96 until it reaches its vertical orientation, as indicated by the arrow 100. By moving the table to the left prior to tilting it, the table top member 12a remains substantially in a central location with respect to the base 10 even after tilting to the vertical mode. This feature thus reduces the area of the "footprint" of the x-ray system by keeping the table top near the center of the base in all configurations. After the table top has been rotated to its vertical configuration, the right hand end panel 20 can be lowered by pivoting in a clockwise direction as shown in FIG. 1 (in phantom) to form a ramp which can facilitate movement of a patient in a wheel chair or walking onto the base.

It can be seen from the drawing of FIG. 6 that, in order to tilt the table from its horizontal to its vertical position, the table assembly must be moved to the left, as shown in phantom in FIG. 6. When the table assembly is moved to the left, to the point shown in phantom, it is then tilted to the vertical in the direction of the arrow 100 by an operator. It should be noted that, during tilting, the table is effectively supported about its pivot axis, which is located near its central portion of the table relative to its longitudinal dimension, and the table does not slide downwardly during tilting, but rather its motion is solely rotational.

Figure 7:
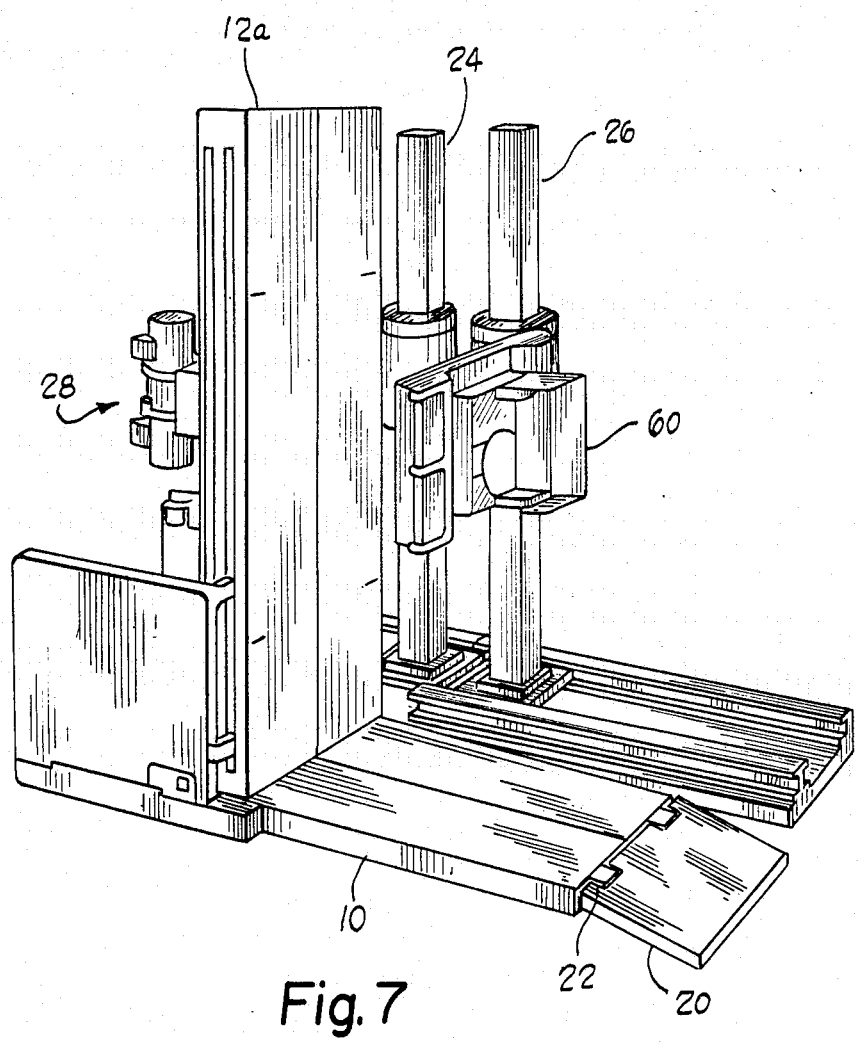
FIG. 7 is an isometric view of a system as shown in FIGS. 1 and 2 deployed in a vertical fluoroscopic configuration.

FIG. 7 illustrates the system of this invention in one of its its operating mode with the table top 12 in the vertical position.

The relative movements of the various components of this system, such as of the tube head, spot filmer, masts, and table top, are controlled by means of electrically and/or mechanically operable locks or brakes of known type, in order to stabilize the positioning of the various movable components of the system with respect to one another to maintain a constant relative orientation of these components appropriate for the particular operating mode selected. For example, sliding motion of the masts along the track 68 is inhibited by solenoid actuable brakes which are in turn actuated by a foot pedal, or by control panel buttons, and which have manual override capability. X-ray table top positioning is also controlled by electric brakes. Motions of the tube head with respect to the mast 24 are controlled by manually operable locks or brakes of known type. Vertical and orbital motion of the tube head and spot filmer about their respective masts are controlled by manually operable locks.

The mast 26, being movable with respect to the mast 24, can be manually moved, or parked, near the right hand end of the track 68 as shown in FIG. 1. This flexibility assists in getting the spot filmer and its associated mast out of the way to avoid interference when radiographic imaging is being executed. Alternately, the mast 26, and all the components carried on it, as well as the carriage member 74, can be removed manually from the system altogether. This is done by removing the mast 26 from the receptacle portion 76, and then by sliding the carriage member 74 off the end of the track 68. Such a configuration is beneficial when the system is to be used as a "radiographic only" system, and fluoroscopic imaging is not desired. This feature also implies that the system S can be provided for radiographic use only by the omission altogether of the mast 26, spot filmer 60, carriage member 74 and the associated components. Where it is desired to practice only radiographic techniques, all these elements can be eliminated entirely. This convertability between a radiographic only, or an R/F, system, in conjunction with the basic concept further enhances the uniqueness of this invention. Other known systems are too integrated to form two distinctly different systems without major design changes.

All movable elements are designed or counterbalanced in a manner to permit easy manual movements. No cranks, or mechanisms providing mechanical advantage, or power assists are used in this embodiment. However, these components can be powered or counterweighted using methods known to the state of the art.

An in table cassette cabinet, commonly referred to as a bucky, is incorporated in the table top assembly.

Figure 8:
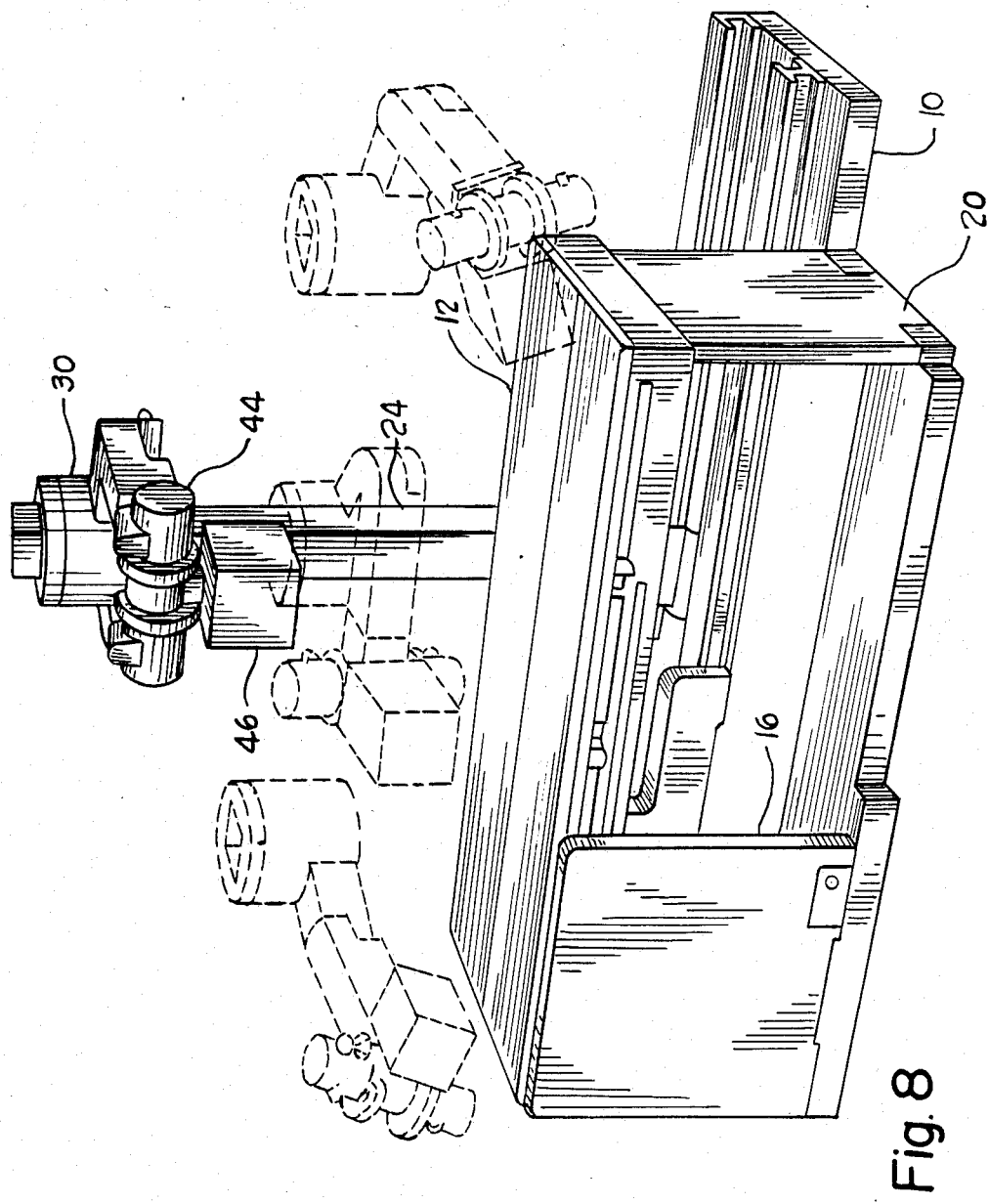
FIG. 8 is an isometric view of a system as shown in FIGS. 1 and 2 adapted for use in a radiographic only operating mode.
Figure 10B:
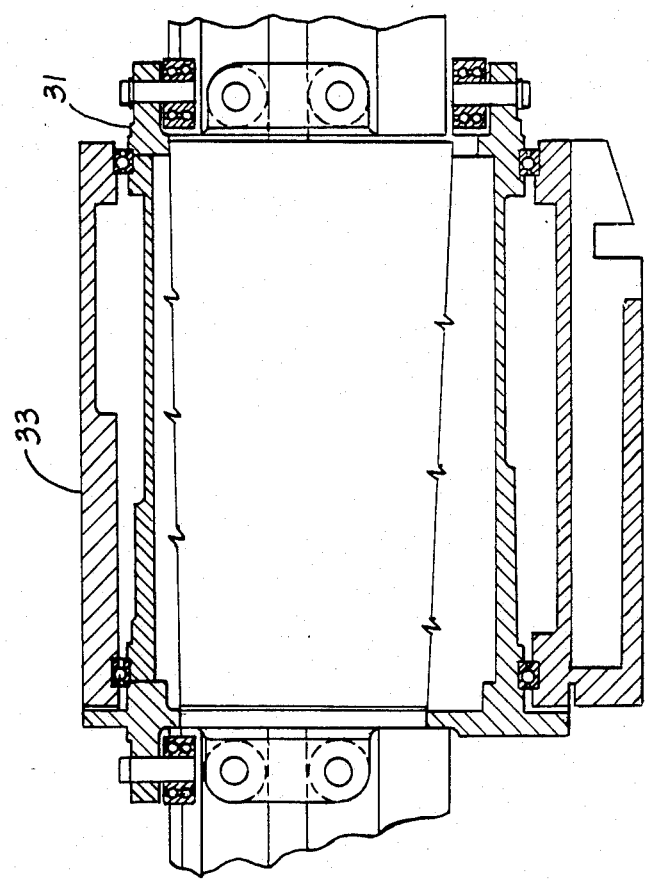
FIGS. 10 and 10A are detail drawings illustrating a portion of the system illustrated in FIGS. 1 and 2, and FIGS. 11-13 are illustrations showing simplified additional embodiments of the present invention.
Figure 10A:
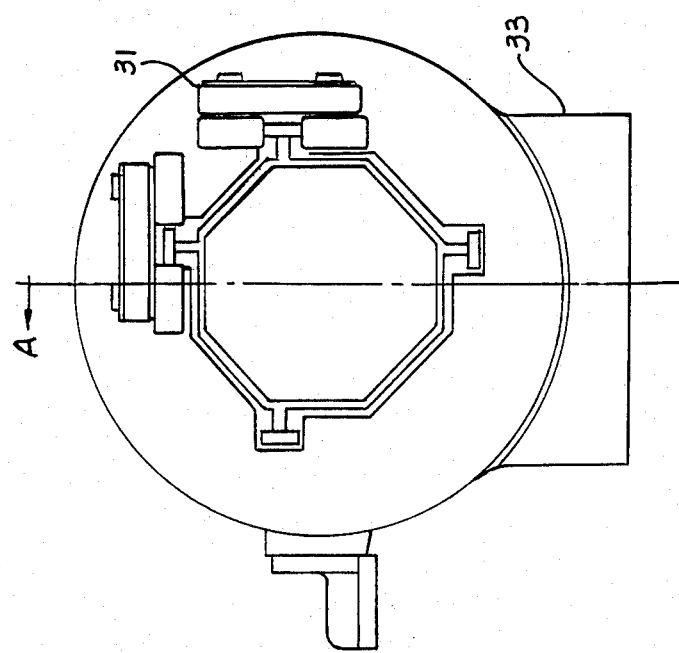

FIG. 8 illustrates the system of this invention operating in its so-called "radiographic only" configuration. Note that in this configuration the advantages of the offset x-ray tube support arm and central pivoting table concept continue to result in the advantages of a short length system with enormous patient coverage and procedure capability. In this configuration, the product portability is increased and packaging volume and weight is reduced.

This convertibility feature allows the user to deploy an R/F system as radiographic only or with the fluoroscopic feature without resorting to ordering different versions from the manufacturer. This again enhances the utility.

Another unique advantage of this system is the resulting ease of movement of the various components during change from one clinical procedure to another. Due to the fact that the spotfilmer and its associated mast can be parked, it is not necessary for the the user to move the fluoroscopic payload when doing radiographic procedures along with the radiographic payload. For example, if both the radiographic unit and spotfilmer were coupled to a single mast ("C" arm configuration) both units would be moved in all procedures. Furthermore, the tendency for damage is much greater with movement of massive and cumbersome "C" arms in both rotation and translation, especially in tight quarters such as a military isoshelter.

The present system is designed to be manually knocked down and reassembled without the aid of tools. That is to say, wherever fastening and unfastening of components one from another is required, that fastening is provided by the use of hand acutable apparatus, such as snap locks, hand operable screw apparatus, and the like.

The system of this invention is modular in nature, in that it can be broken down into subassemblies which can be stored in resuable containers, each dedicated to a particular subassembly or subassemblies, for transport. Each of the subassemblies is designed to be sufficiently light in weight to be handled efficiently by a team of four men.

As mentioned above, the base member 10 is of a segmented construction, the segments of which are hinged together for folding for easier transport.

The system S is transportable in 13 containers. Each container is dedicated for storage of predetermined system components. Generally speaking, each container comprises the same kinds of material, fasteners, packing material and other components. Aspects of the containers are illustrated in FIGS. 9A–9C. Referring to FIG. 9A, a container 150 includes a top portion 152 and a bottom poriton 154. Each container top portion includes packing material glued therein, and positioned appropriately to maintain stored system components in a desired orientation within the container 150. The packing material is illustrated, for example, in FIGS. 9B and 9C at reference character 156. Each container bottom also includes packing material glued appropriately to its inside surface. The packing material 156 includes polyethylene foam.

Fasteners, such as at 158 in FIG. 9A, are provided to selectively hold together the top and bottom portions of the container 150. Each fastener includes a clamp riveted to the container bottom and a keeper riveted to the container top. A clamp guard riveted to the container bottom protects the clamp when the container is closed.

Handles, such as at 160, 162 are provided at either end of the container 150 to assist in facilitating hand carriage of the container. Each handle is held in position by a bracket which is riveted to the container.

A gasket 166 is located in the edge frame of the container top. When the container is closed, the gasket forms a water-tight seal.

A pressure relief valve 168 is provided in each container, which automatically opens to equalize the pressure inside the container with ambient pressure.

Certain simplified embodiments of a system such as described above also yield important advantages without resort to the complexity of the system described in FIGS. 1-4. Such a system is illustrated in FIG. 11.

Figure 11:
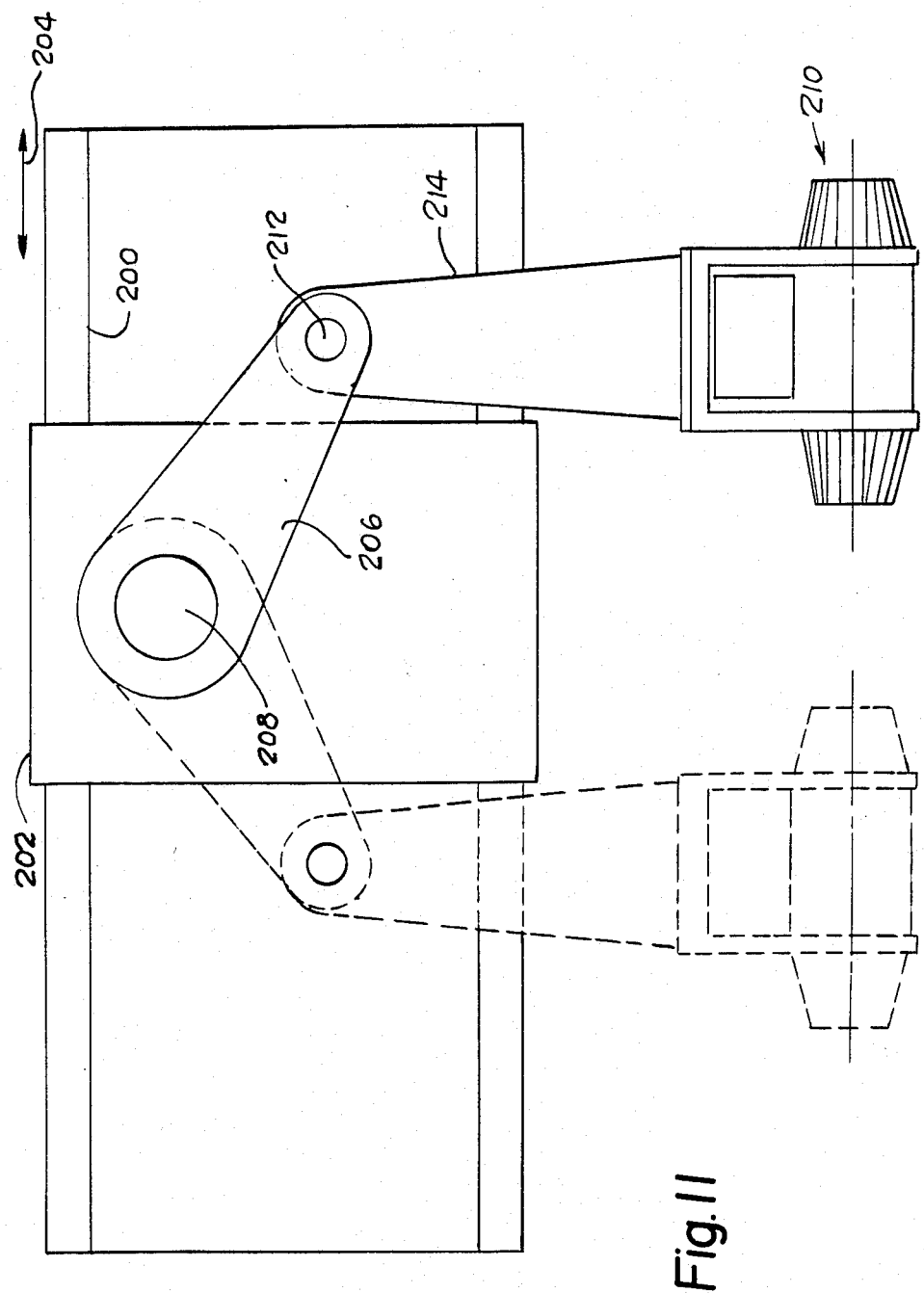

FIG. 11 illustrates a track structure 200 upon which rides a carriage member 202 which is movable in a direction given by the arrows 204. An arm 206 is pivotally mounted to the carriage for rotation about an axis described by a pivot point 208. An x-ray source 210 is mounted for rotational movement with respect to an axis 212 parallel to the pivot axis 208 and extending through the arm 206. In the instance of FIG. 11, the x-ray source 210 is coupled for rotational movement about the pivot 212 by an arm 214. It is to be understood, however, that the x-ray source 210 could be positioned such that a pivot axis 212 passes through the source, i.e., the x-ray source could be directly pivotally mounted to the arm 206.

A very decided advantage results from this structure. The x-ray source 210 is offset from the pivot axis 208 by a distance equal to the distance between the pivot axes 208, 212. This means that the total possible excursion of x-ray tube motion in a direction parallel to the arrows 204 is considerably longer than the length of the track structure 200. This feature thus enables x-ray source coverage over a distance substantially longer than the track structure to which it is ultimately mounted. This double pivot arrangement thus enables the use of relatively short tracks, which occupy relatively little area, while still retaining flexibility of motion of the system.

Figure 12:
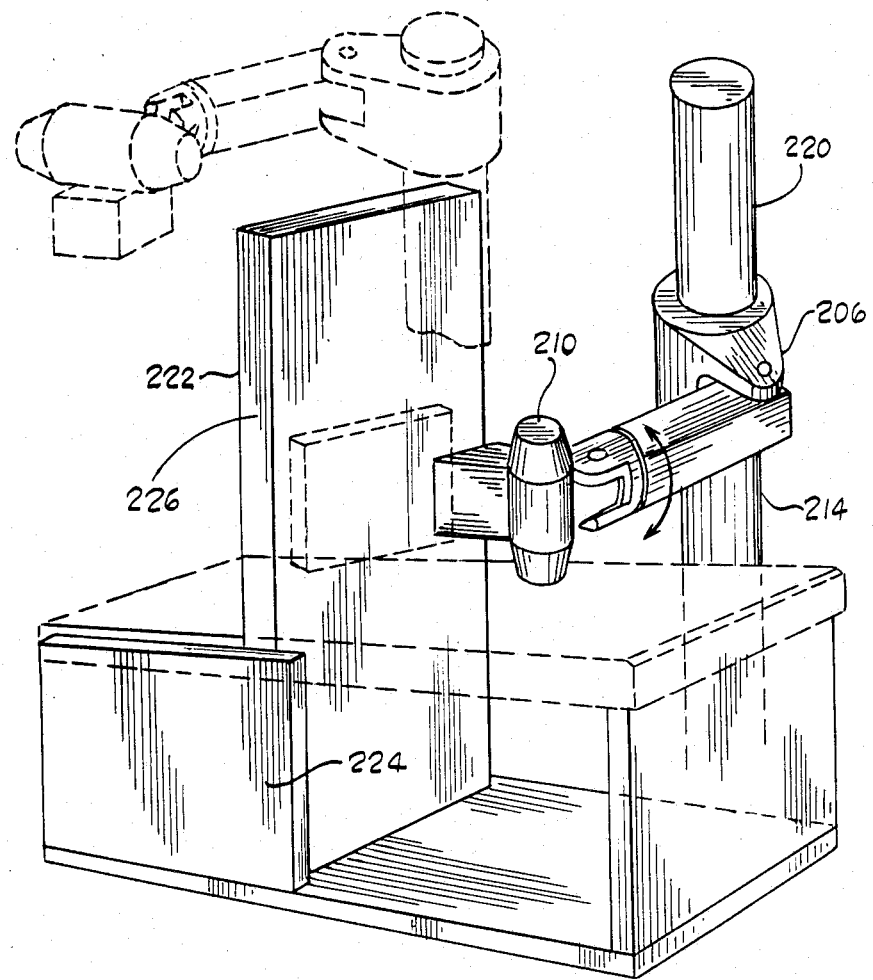

FIG. 12 illustrates an embodiment corresponding to that of FIG. 11, but with some additional elements. In FIG. 12, the arms 206, 214 are mounted for rotation on a mast 220 which in turn is mounted for longitudinal motion on a track similar to that described in connection with FIGS. 1 and 2. The x-ray source 210 is mounted for pivotal motion about an axis which is substantially coincident with the axis of the second arm 214. A patient support means, in this case an elongated table 222, is also provided. The table 222 is supported for pivotal movement between horizonal and vertical positions, about a pivot axis 224, which is generally centrally located with respect to the longitudinal dimension defined by the table's shape, the pivot axis being horizontal.

Thus, the embodiment of FIG. 12 adds to the embodiment of FIG. 11 the additional features of pivoting the tube about the axis of the second arm, and pivoting the patient support table about an axis near its center with respect to its longitudinal dimension. The provision of the tiltable table with the pivot apparatus centrally located, combined with the two-pivot apparatus of FIG. 11, results in a system which further minimizes the length of the overall area "footprint" required to achieve x-ray tube movement with respect to the patient for varying S.I.D.

Optionally, an in-table cassette carriage, or "bucky" 226 can be added to the table 222.

Tilting the table in its central region, rather than at one end or another, as done in the prior art, combines with the other features of the FIG. 11 embodiment to further minimize the amount of longitudinal length required to operate the system in many different modes. As shown in FIG. 12, the tube can project a horizontal beam from either side of the vertically positioned table, and from a variety of distances in each direction. The system of FIG. 12 is also capable of doing lateral work, wherein the x-ray beam is projected horizontally, transverse to the table top.

In accordance with a further embodiment, the embodiment of FIG. 12 can be enhanced by the addition of pivot means, such as described in connection with FIG. 4, for mounting the x-ray tube for pivotal motion about a pair of orthogonal axes both orthogonal to the axis defined by the second arm. This added mechanism results in a radiographic system capable of a wide range of x-ray source positioning and beam angles, including for oblique work. Counting the tiltable patient support means, the apparatus of FIG. 12, thus enhanced, provides no less than six different types of rotational tube/-patient relative motion, as well as linear motion made possible by the track mounted mast.

Figure 13:
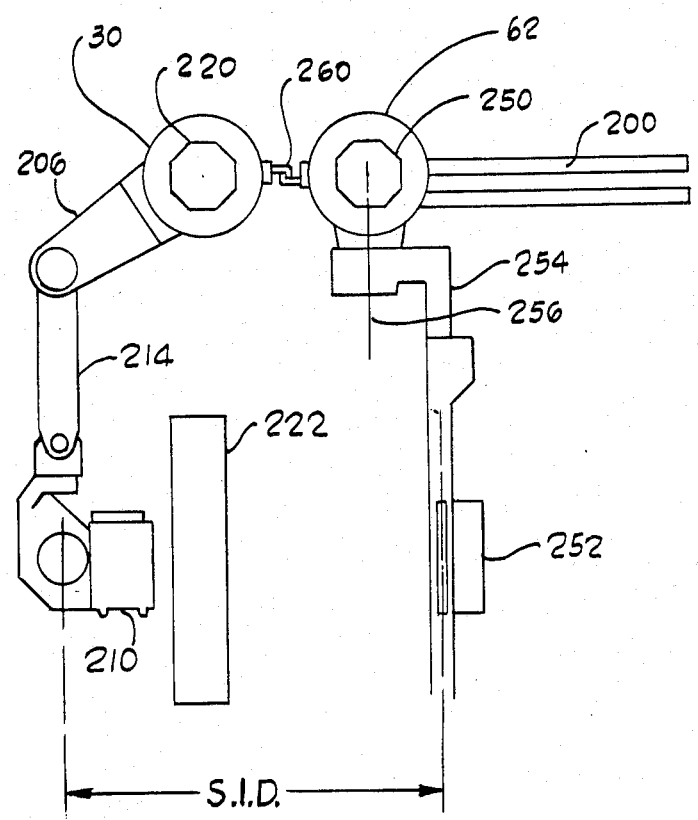

Flexibility of the system of FIGS. 11 and 12 is further enhanced by adding apparatus as shown in FIG. 13. FIG. 13 illustrates the addition to the system of a separate mast 250, and a filmer device 252 coupled to the mast 250 by way of a rotatable arm structure 254. Alternately, the arm 254 can carry a fluoroscopic device.

As described in connection with previous embodiments, the mast 250 is movable longitudinally along the guide structure which defines a path parallel to the longitudinal dimension of the table top.

An important aspect of this embodiment is that the arm structure 254 can offset the fluoro device or filmer device with respect to the masts. In the plan view of FIG. 13, the arm 254 is rotatable about a horizontal axis 256 which intersects the axis of the mast 250. The arm structure 254 can be rotated about the axis 256 to place the fluoro device carried on the arm 254 more distant from the table top than the mast 250. Thus, the offsetting of the fluoro device from the mast 250 enables a greater S.I.D. than would be possible if the fluoro device were simply coplanar with the axis 256. Thus, in a sense, the offsetting of the fluoro device in effect "extends" the track upon which the mast 250 rides. The fluoro device can be cantilevered out beyond the extent of the track on which the motion of the mast 250 is limited.

Additionally, the entire arm structure 254 is mounted for orbital rotation about the centerline axis of the mast 250.

Great flexibility and compact system size are achieved with the combination of fluoro device/spot film offset and x-ray source offset. For example, when a great distance is needed between the source and the fluoro device, the masts can be moved to opposite ends of the track, and even more separation can be achieved by positioning the source and the spot film device extending in opposite directions in their offset placement mode. For example, if the track is 6 ft. long, and each offset capability is 2 ft., a spread of 10 ft. can be achieved with a track of only 6 ft.

Of course, where the system of FIG. 13 is operated in a vertical fluoroscopic mode, the masts can be coupled together at their minimum spacing for movement in unison, and the offset feature, as described in detail above, enables the precise vertical alignment of the source with the radiation detector. This alignment is maintained, because of the coupling, during all relative motion between (1) the source and fluoro device and (2) the patient table.

Additionally, means 260 is provided to couple the vertical carriage assembly of the source to the vertical carriage assembly mounted on the fluoro mast. These vertical carriage assemblies correspond to the elements 30, 62, as shown in FIGS. 1 and 2. When this is done, and the system operated in a vertical fluoroscopic mode, the x-ray beam maintains its alignement with the fluoro device during vertical movement of the source and fluoro device. Thus, the source and fluoro device move vertically in unison.

In vertical fluoro operation, the system operates with a fixed S.I.D., whereas in horizontal table fluoroscopy the system operates with a variable S.I.D. In this mode, the x-ay tube is stationary vertically while the filmer or fluoro device can be vertically moved. Vertical alignment, however, is maintained because of the coupling between the masts and the offset structure. The pivot capability about the axis 256 and about the central axis of the mast 250 provides additional degrees of rotation of the filmer to allow unique park positions wherein the filmer can be swung out of the way to any of a plurality of park positions, such as the the rear of the table. In many prior art systems, the filmer remains somewhat over the table when in the park position, and encumbers radiographic procedures.

The versatility of the present system is expressed in concrete terms by the following list of the types of radiographic and fluoroscopic studies which can be performed with the present system, which is lightweight, as well as relatively compact, and without the aid of any other equipement:

RADIOGRAPHIC/FLUOROSCOPIC PROCEDURES

1. Fracture of vault of skull (consciousness)
2. Fracture of face bones
3. Fracture and fracture dislocation of spine w/o cord lesion
4. Fracture of ribs
5. Fracture of pelvis
6. Fracture of clavicle
7. Fracture of scapula
8. Fracture of humerus
9. Fracture of radius-ulna
10. Fracture of handbones
11. Fracture of femur
12. Fracture of tibia-fibula
13. Fracture of tarsal-metatarsal
14. Dislocation of shoulder
15. Dislocation of elbow
16. Dislocation of wrist
17. Dislocation of hip
18. Dislocation of knee
19. Dislocation of ankle
20. Disloation of cervical spine
21. Dislocation of spine, complications
22. Brain laceration and contusion w/wound
23. Intracranial hemorrhage w/o pen. or perf. wound
24. Intracranial hemorrhage w/wound
25. Traumatic pneumo and hemo chest thorax w/o pen. or perf. wound
26. Traumatic pneumo and hemo thorax w/wound
27. Lung injury w/o open wound
28. Lung injury w/open wound
29. Gastrointestinal tract w/open wound
30. Liver injury w/open wound
31. Liver injury w/o open wound
32. Spleen injury w/open wound
33. Spleen injury w/o open wound
34. Pelvic organ injury w/open wound
35. Open wound back w/o complications
36. Open wound, head, neck and trunk w/o complications
37. Traumatic amputation arm and hand w/o complications
38. Open wound, hip, and thigh complications
39. Open wound, knee, lower leg, and ankle w/o complications
40. Open wound, foot w/o complications
41. Traumatic amputation foot w/o complications
42. Traumatic amputation leg w/o complications
43. Multiple open wounds, upper extremities w/o complications
44. Multiple open wounds, lower extremities w/o complications
45. Burn, face, head, and neck 2 w/o complications
46. Burn, face, head, an neck 3 w/o complications
47. Burn, trunk 2 w/o complications
48. Burn, trunk 3 w/o complications
49. Nerve injury-spinal cord, cervical w/open wound
50. Nerve injury-Thoracic and Lumbar spine cord w/open wound
51. Nerve injury-sacral spinal cord w/open wound
52. Pulmonary tuberculosis
53. Meningococcal infection (includes meningococcal meningitis)
54. Gas gangrene (various extremities)
55. Aseptic meningitis/encephalitis
56. Malignant and benign neoplasms (affected past)
57. Diseases of the ear and mastoid process
58. Diseases of veins and lymphatics and other vascular diseases
59. Hernia
60. Other diseases of intestine and peritoneur A particular embodiment of the table base assembly is illustrated in FIG. 14.

According to this embodiment, a segmented base includes three separate aluminum composite honeycomb panels 300, 302, 304. Each of these panels consists of an aluminum honeycomb core, covered by an aluminum skin bonded to the core. Each panel also includes aluminum frame structure bonded to the outer skin about the perimeter of the panel.

Figure 14:
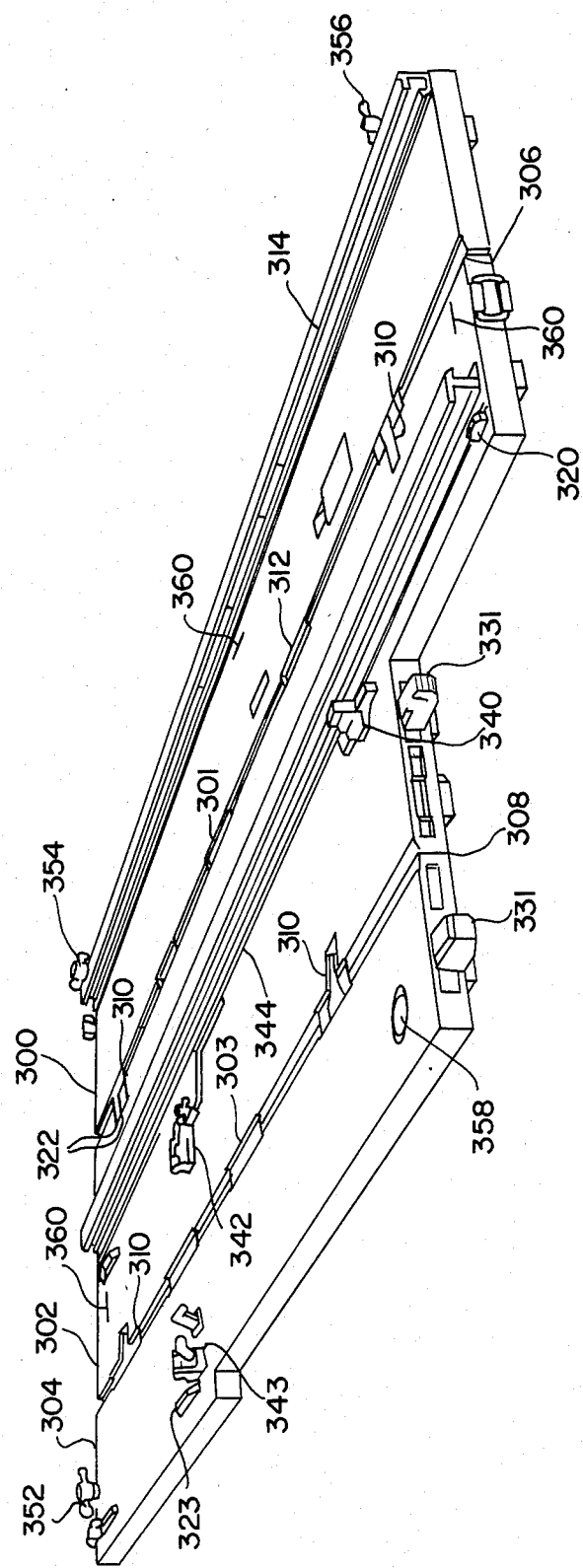
FIG. 14 is an isometric view of an alternate embodiment of a base assembly comprising the apparatus of this invention.

Each of the base segments or panels is joined to its adjacent panel or panels by means of hinges such as illustrated at 306, 308 of FIG. 14, located on the underside of the base assembly when deployed. Each hinge body portion is co-extruded from, and integral with, the aluminum material comprising the frame of its respective adjacent base segment or panel. This is described in greater detail in connection with the discussion of FIG. 21 below.

The pins of the respective hinges can optionally be made removable, such that the base panels can be completely separated one from another, if requirements of packing and/or transport so require or indicate.

Another significant attribute of the hinge joints between panels is that they are provided with adjustable compression stops recessed in the upperside of the base panels, to precamber, or bias, the panels into a slightly upwardly bowed configuration, such that imposition of the payload on the base will result in zero camber, and thus the base will be rendered substantially perfectly flat when its payload is assembled on it. This aspect will be further discussed in connection with FIG. 23 below.

When the X-ray system of this invention is to be deployed, the hinged 3-panel base assembly is opened flat and then secured by four removable hinge fasteners or clamps indicated, for example, at reference character 310 of FIG. 14. The clamps 310 serve to lock the base panels together relative to each other in a substantially rigid and flat configuration. Each of the clamps, as shown in FIG. 17, is, when locked, located in a recess 310a in the surface of the base and is generally flush with that base surface.

Figure 17:
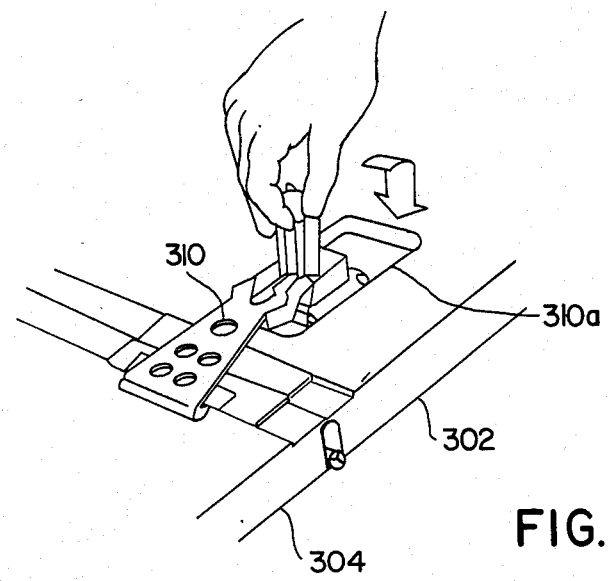
FIG. 17 is an isometric drawing of details of a clamp component illustrated in FIG. 15 for use with the base assembly.

Details of such a clamp are illustrated in FIG. 17.

The assembly as described thus far forms the platform which secures and supports the complete table and radiographic mast assemblies and, as required, imaging subsystems.

Tracks 312, 314 provide guideways for the radiographic mast and, if installed, a fluoro mast as well. End stops, such as 320, and stop release mechanism such as 322, limit the travel of the mast carriages in the tracks. The stop release mechanisms, when held down, permit the horizontal mast carriages, described above, to be installed or removed from the base.

Figure 20:
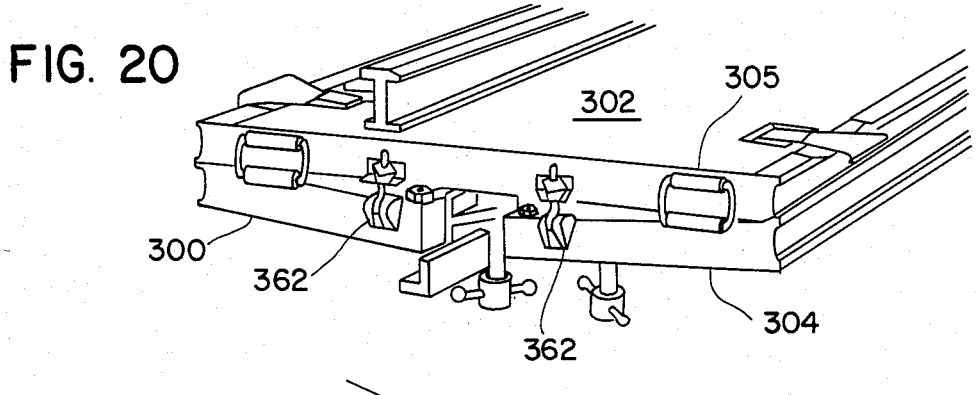
Figure 20A:
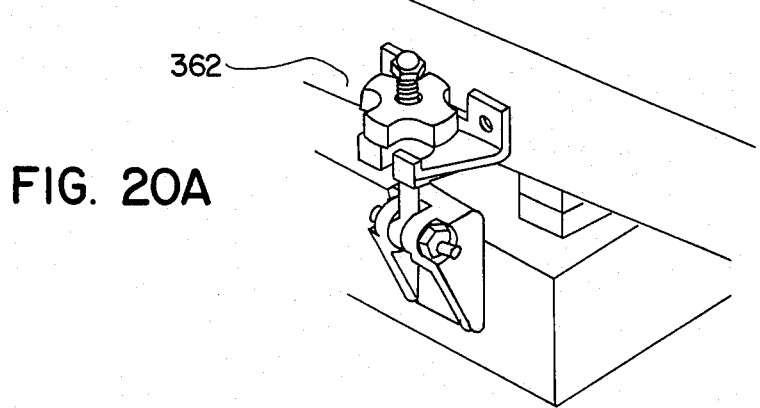

Leveling of the base during deployment (FIG. 14) is facilitated by adjusting four threadedly adjustable feet extending beneath the base at its respective corners, and handles of which are shown generally at 352, 354, 356, 358. While design of the specific embodiment for the adjustable leveling feet is believed within the ordinary skill in the art, details of the leveling feet are shown in FIG. 20, including a T-bar handle 355 whose rotation adjusts the extension of a foot 357 below the base. Note that the leveling foot assembly 358 is recessed within the base segment 304 to eliminate a trip point at a location on the base over which operators and patients are likely to frequently pass and does not utilize a T-bar handle but is adjusted by rotation of the foot 357.

Three spirit-type bubble center leveling indicators, shown at 360 of FIG. 14, provide an indication of the attitude of the base with respect to the horizontal, to assure accurate leveling.

FIG. 20 shows the articulated panel base assembly folded for storage. Transport latches (shown in detail in FIGS. 2-18), such as at 362, are provided to secure the front and rear base sections 300, 304 to the center section 302. Four handles, such as shown at 305 in FIG. 20, two installed at each end of the base center section panel 302, are provided to facilitate lifting of the base in and out of a container, and for positioning the base during deployment or disassembly. Preferably, the handles are spring loaded to the stored, or compact, position, relative to the base portion 302.

Figure 21:
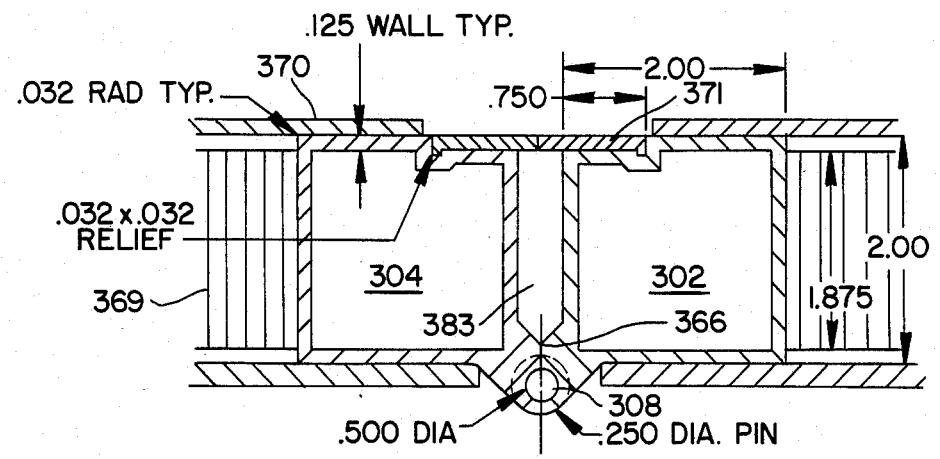
FIG. 21 is an elevational view illustrating detail of a portion of the base assembly shown in FIG. 15.
Figure 22:
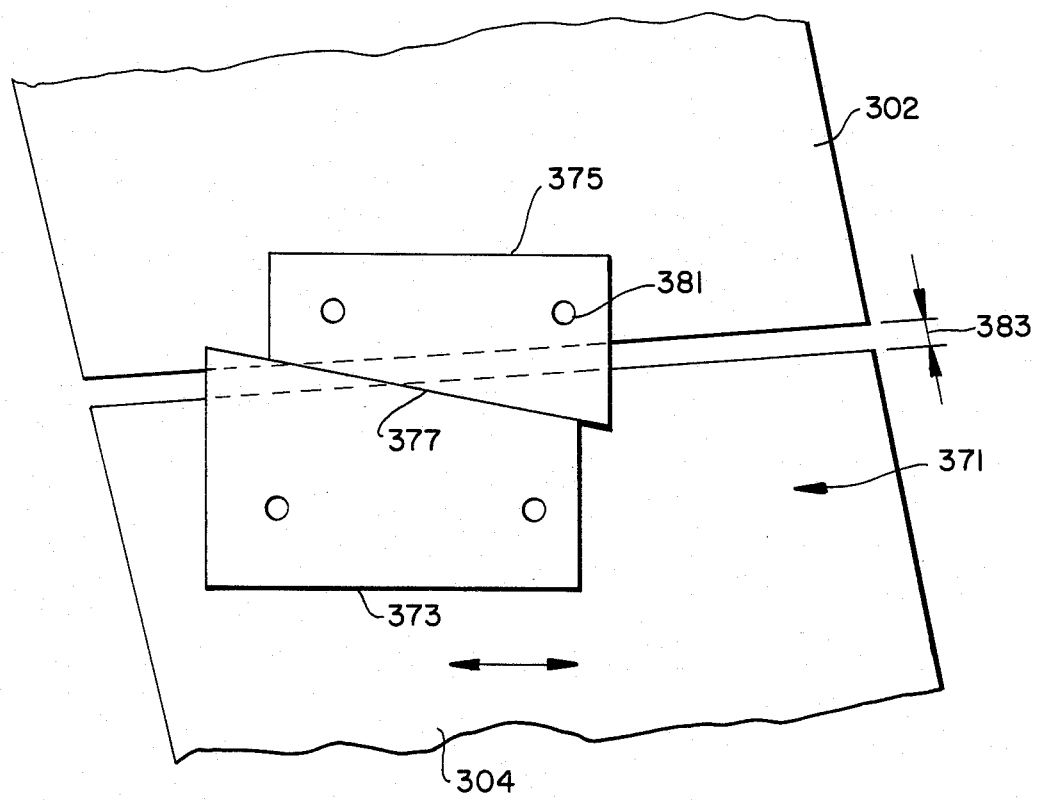
FIG. 22 is a plan view of a detail of the base assembly shown in FIG. 15.

FIGS. 21 and 22 illustrate details of construction of the hinges which hold together the base panel sections. FIG. 21 is a cross-sectional view of such a hinge. The hinge illustrated there is one of the hinges 308, joining base panels 302 and 304. The cross-sectional view shows the inner core of the base panels, generally at 369, and also the outer aluminum skin 370. The inner core can be a aluminum honeycomb or other light weight, low density core material. Also illustrated is the aluminum extensions 366 of the frame forming the edge, or corner, of the base panel. As can be seen from FIG. 21, the hinge body parts, through which the hinge pin extends centrally, are integral with, and in fact are co-extruded with, the frame portion along the common edge, or corner, of the respective base panel.

FIG. 22 illustrates one of the compression stops designated generally as reference character 371. The location of the stop 371 is also illustrated at the top of FIG. 21, where the stop is illustrated as nested in mating recesses in the top of the two adjacent base panels 302, 304.

The stop means 371 includes two flat plates 373, 375, each of which is fastened to one of the adjacent base plates 304, 302, respectively. The fastening can be by rivets, screws or other means. Each of the plates 373, 375 defines an inclined edge facing its neighbor. The inclined edges abut one another to define an interface 377 therebetween.

It can be seen from FIG. 22 that the relative position of the two plates 373, 375, in the direction of the arrows in FIG. 22, defines the degree of separation 383 between the adjacent plates. In manufacturing the base assembly, the relative positioning of the plates 373, 375 is adjusted to obtain the desired spacing 383. When this desired spacing is obtained, the plates 373, 375 are then fastened to the neighboring base panels 304, 302.

By reference to FIGS. 14, 21 and 22, it can be seen that the camber, or inclination, of the base panels 304, 302, 300 with respect to one another can be adjusted by appropriate location of the relative positions of plates such as 373, 375. In practice, there are four such compression stops along the joint between panels 304 and 302, and there are five such compression stops along the joint between panels 302 and 300.

Tests have shown that a desirable precamber of the base assembly, effected by appropriate relative adjustment of the compression stop elements during assembly, leaves the base assembly slightly upwardly bowed. More specifically, a desirable precamber, or bowing, leaves the panel 302 elevated approximately 1/16" above a flat surface on which the base assembly is laid, without the imposition of any additional component weight or payload on the base. It has further been found that, if this condition is observed, the imposition of approximately 1000 pounds of components and payload on the base causes the base to assume a configuration of zero camber, i.e., substantially flat.

FIG. 22 illustrates holes, such as 381, which are designed to accommodate rivets or other fasteners to fasten the plate 373, 375 to the adjacent base panels.

Optionally, the holes 381 can be made in the form of slots, to allow for adjustability of the lateral position, in a direction of the arrows in FIG. 22, of the respective plates 373, 375 relative to their associated base panels 304, 302.

Recapitulating, then, the compression stops enable one to bias the base assembly structure in a direction such that, when the structure is deflected under predetermined load, the structure returns to a zero bias, or zero camber.

The X-ray table, which supports the patient, not shown in FIGS. 14 et seq., is supported by left and right table end supports.

Figure 15:
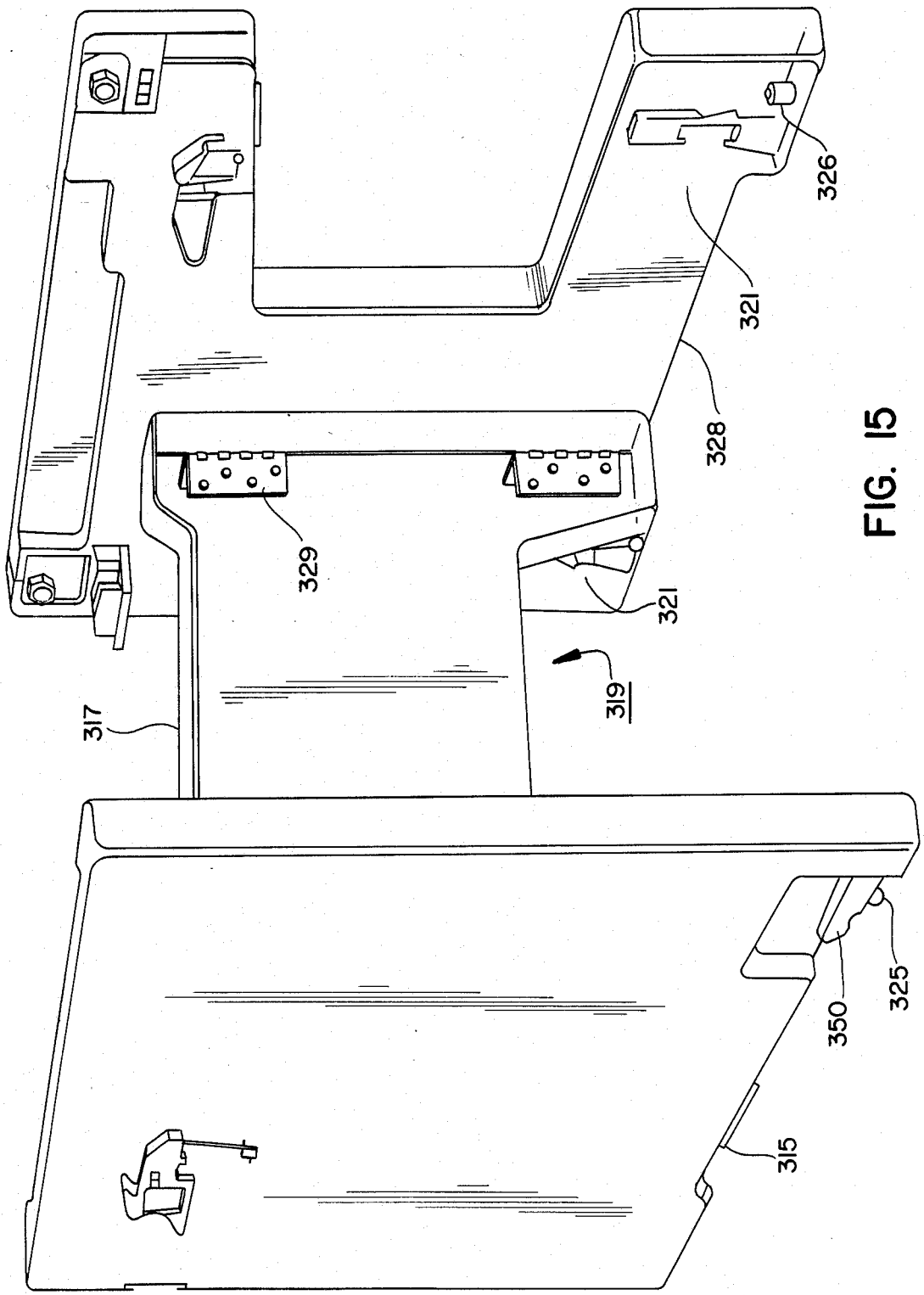
FIG. 15 is an isometric view of a table support component adapted for use with the base assembly of FIG. 14.
Figure 16:
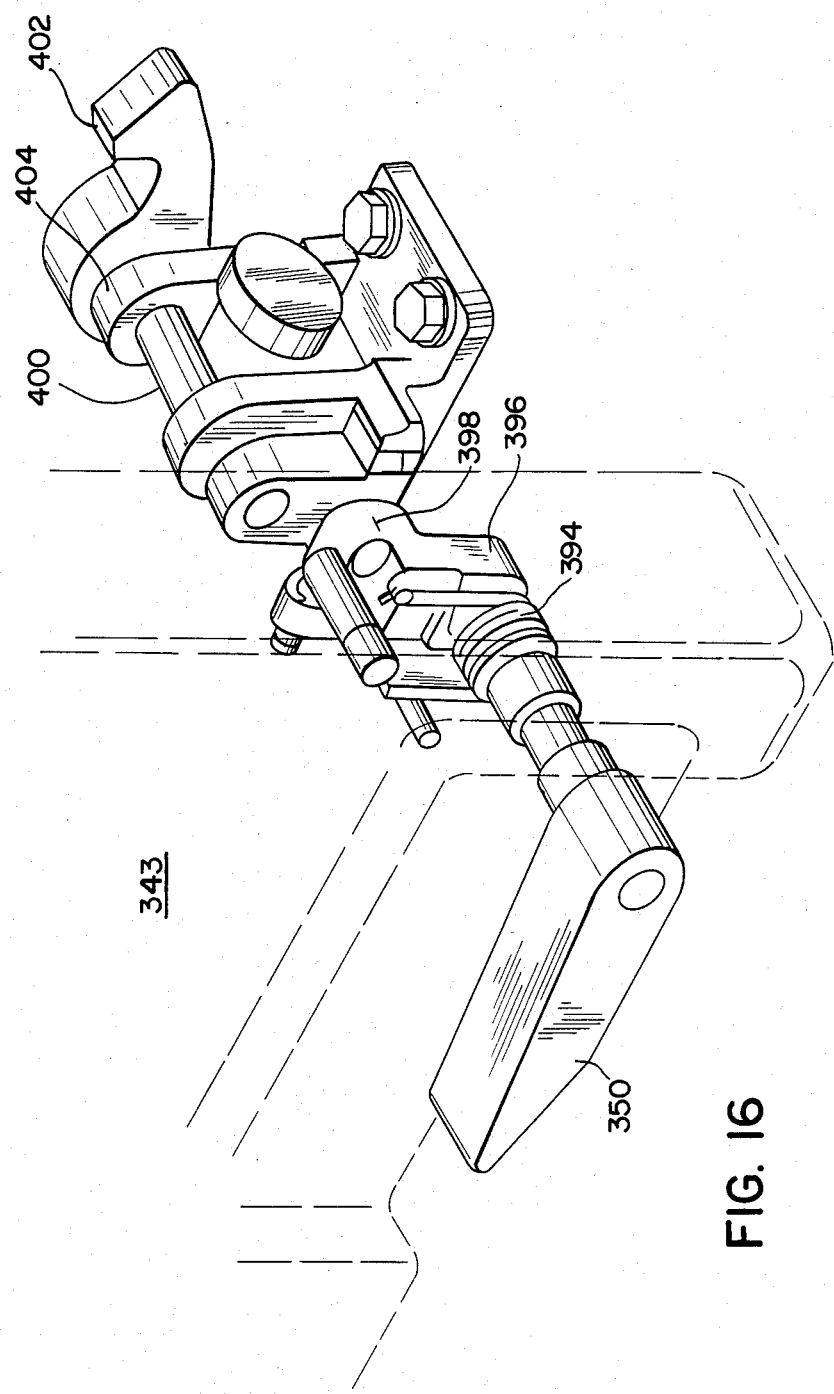
FIG. 16 is an isometric drawing of a detail of the base assembly shown in FIG. 14.

FIG. 15 illustrates generally the left end X-ray table support assembly 319. FIG. 16 illustrates a detail of an associated latch.

The left end support assembly comprises three foldable hinged sections. This includes a front section 315 (foam core with carbon fiber skin), a center section 317 (foam core with glass fiber skin) and a rear section 328 (foam core and carbon fiber skin), joined by hinges such as indicated at 329. When assembled, as can be seen from FIG. 15, the left end table support assembly describes generally an "H"-configuration. The front and rear sections are hinged to fold compactly upon the center section, such that there is no overlap between the front and rear sections, and the thickness of the folded configuration is only the sum of the thicknesses of the center section plus the thickness of one of the front and rear sections.

The left end table support assembly is engaged by four base clamps, one of which is indicated generally at 321 of FIG. 15. The base clamps engage support clamp brackets, illustrated for example at 323 of FIG. 14. To accurately locate the left end table support, mating dowel studs, such as 325, and bushings such as 326 are provided on the left end table support assembly and the base, respectively.

When the left end support 319 is in place on the base panel 304, as shown in FIG. 15, a front latch 343, for releasably holding the X-ray table in a vertical position, is released by operating a left end support toe pedal 350 (see FIG. 16) to allow the table top assembly to be lowered from the vertical to the horizontal position.

The toe pedal 350 acts in conjunction with the front table latch assembly 343 on the table base. The pedal is spring loaded to the up position by a spring 394, as shown in FIG. 16. When the left end support is installed on the base, a latch drive cam 396 engages with a mechanical coupling 398. When the toe pedal is depressed, a latch shaft 400 rotates to release a latch pawl 402 from the table frame if the X-ray table top is in its vertical position. Stop means 404 maintains the latch pawl in engaged position. The design of the toe pedal assembly is such that it automatically couples with the front table latch when the left end support 319 is positioned on the table base assembly.

It is to be noted that the rear portion 328 of the left end table support has an inset cut from it, forming generally a "C"-configuration. This inset facilitates movement of the X-ray tube substantially along the entire length of the X-ray table when the tube is in its undertable position.

A right end support latch 340 and a rear table latch 342, are interfaced by a flexible cable 344, as shown in FIG. 14. As will be described in more detail below, the right end support latch 340 serves to releasably lock the right end support in a vertical position. The rear table latch 342 serves to releasably hold the table in a vertical position. The flexible cable 344 extends between the right end support latch 340 and the rear table latch 342, and releases the rear table latch 342 only when the right end support latch 340 is locked to the right end support, in a manner described in more detail below. This feature prevents the table top from being lowered from a vertical to a horizontal position unless the right end support is locked in place.

Figure 18:
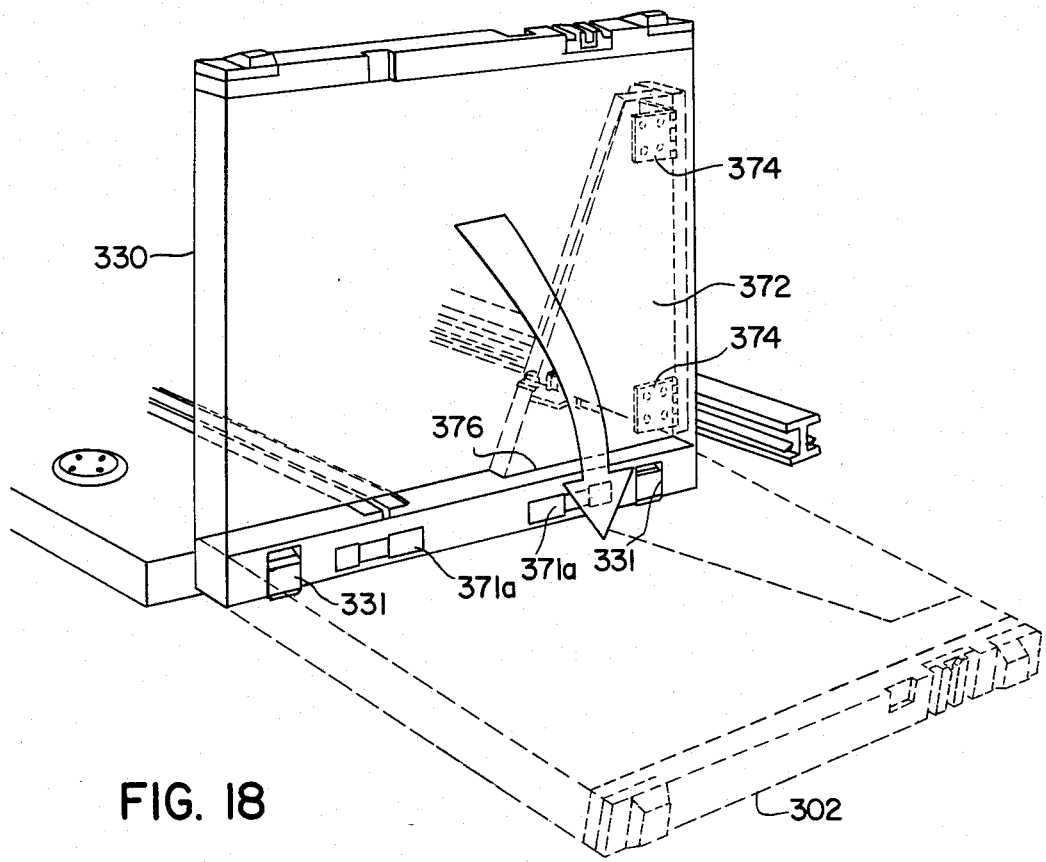
FIG. 18 is an isometric drawing illustrating another support component for use with the base of FIG. 14.

The right end table support 330 is illustrated in FIG. 18.

The right end table support 330 is a foam core fiber reinforced skin composite material which supports the right end of the X-ray table top when the top is in its horizontal configuration. When the table top is vertical, the right end support can be rotated clockwise, as shown in FIG. 18, to improve operator access to the table and to also provide a wheelchair ramp extending from the ground to the flat upper surface of the base assembly.

The right end support is attached to the base by latch assemblies 371A, each having a retractable pin and being of a quick-release type. When closed, the latch assemblies engage table base hinge brackets 331, and allow the right end support to pivot. With the pins retracted, the complete right end support 330 can be removed altogether from the table base structure without the use of tools.

A wing support 372 is hinged to swing away from the right end support and to provide structural rigidity to the support 330 when the support 330 is in its vertical position As such, it operates in somewhat the same way as a gate leg. Held by two hinges 374 to the right end support 330, the wing support folds flush into a molded recess 376 in the support 330. The wing can be locked to the base by means of the right end latch structure 340, shown in FIG. 14. The right end support 330 comprises a foam core and a glass fiber skin.

Figure 18A:
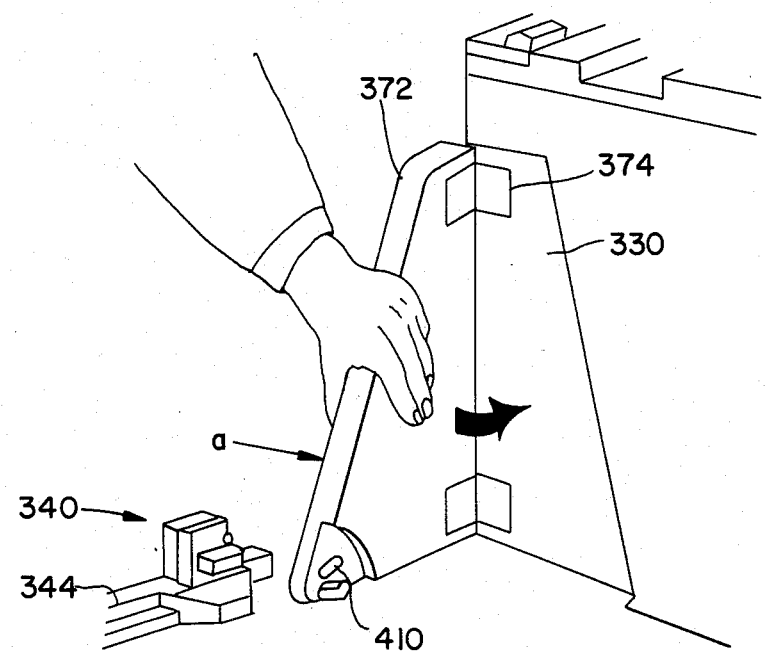
FIG. 18A and 18B is an isometric drawing of a detail of the support shown in FIG. 18 and of a latch component of the base assembly shown in FIG. 15.
Figure 18B:
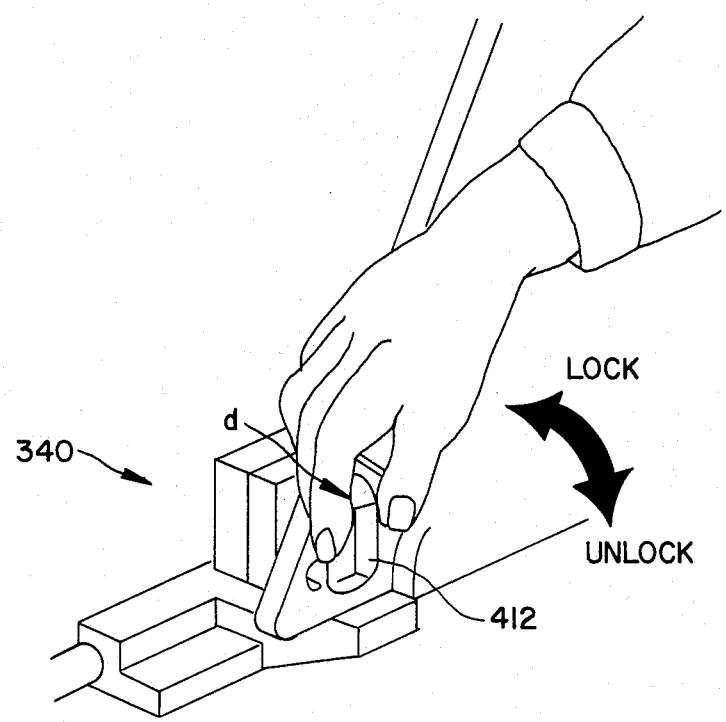
Figure 19:
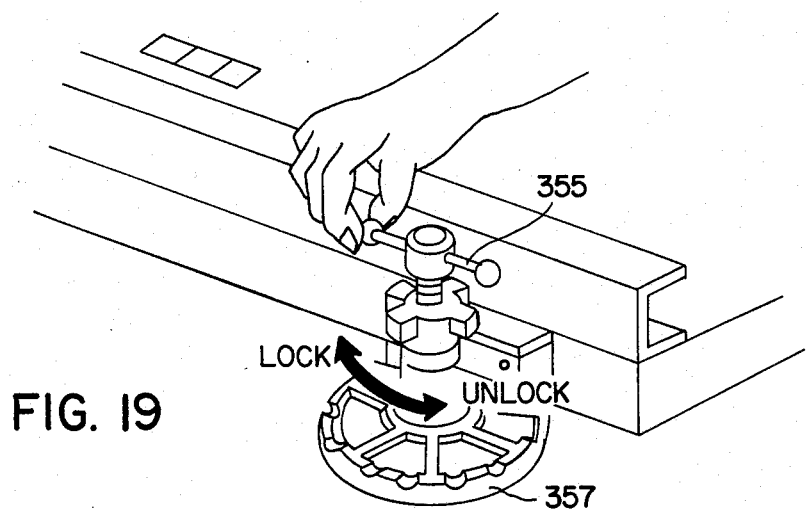
FIG. 19 is a detail drawing illustrating a component of the base assembly shown in FIG. 14.

Some detail relating to the means for locking the wing support to the base is shown in FIG. 18A. That figure illustrates the wing 372, hingedly mounted on the support 330 such that, when the outer end of the wing is swung outwardly, perpendicular to the support 330, it comes into engagement with the right end support latch 340. Note that the outer end of the wing 372 defines an elongated hole 410. The hole 410 cooperates with a generally T-shaped member 412 (see FIG. 19B) associated with the latch 340. When in a generally horizontal position, the T-shaped head 412 can pass through the hole 410 on the wing. The wing is then locked by rotating the head 412 90°.

Figure 18C:
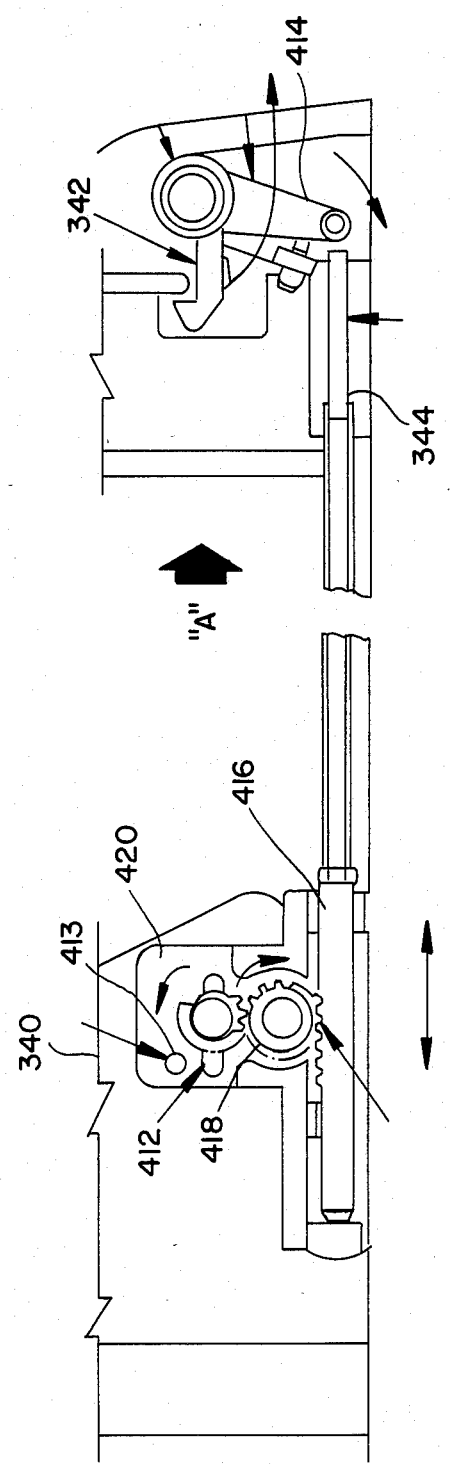
FIG. 18C is a detail plan view of apparatus for establishing interlock between the support component of FIG. 18 and a latching component of the base assembly shown in FIG. 14.

Details of the interlock are shown in FIG. 18C. The T-shaped member 412 is coupled to a wing latch knob which can be rotated from the unlatched or horizontal, position, 90° counterclockwise to its latched, or vertical orientation, providing that the support wing 372 is correctly positioned. A plunger 413, depressed by the wing 372 when in its proper position for latching, prevents rotation of the member 412 unless so depressed. When the member 412 is rotated, it causes rotation of a pinion 418 and translation of rack 416 which in turn moves the flexible cable 344 to correspondingly move lever 414 which in turn unlatches the rear table vertical latch 342 to free the table itself for movement from its vertical to its horizontal position, since the right end support 330 is properly in its vertical attitude and locked to the base to prevent further motion.

All the main components of the apparatus described in this disclosure are made of composite sandwich design. A composite sandwich member consists of a light weight structural core material adhesively bonded between relatively thin high-strength faces, thus producing a panel which has a very high strength to weight ratio.

It is to be understood that the foregoing detailed description is intended as illustrative, rather than exhaustive, of the invention. It is to be recognized that those ordinary skill may be able to make certain additions to, deletions from or modifications to the embodiment described above without departing from the spirit or the scope of the invention as expressed in the appended claims.

We claim:

1. A portable X-ray imaging system including:
   (a) a base assembly;
   (b) an X-ray table member;
   (c) apparatus for detachably mounting said table member above said base assembly;
   (d) an X-ray source;
   (e) means for sensing X-rays to form an image;
   (f) means for mounting said X-ray source and said X-ray sensing means on opposite sides relative to said table member when mounted on said base assembly, and (g) said base assembly comprising a plurality of panels and hinges joining said panels together along edges, said hinges comprising means for facilitating manipulation of said base assembly between a folded stacked configuration and an unfolded substantially flat configuration, said base assembly, when in its unfolded flat configuration being sufficiently expansive to accommodate the mounting thereon of said table member, said X-ray source, said X-ray sensing means and said means for mounting said source and sensing means all within the foot print of said base assembly in its unfolded configuration.

2. The system of claim 1, further comprising:
means for biasing said panels to exhibit upward bowing when laid upon a flat surface, prior to mounting of said table, source, or sensing means on said base assembly, and to assume a substantially flat configuration when a predetermined payload is placed upon said base assembly.

3. The system of claim 1, wherein said hinges are biased by compression stops to compensate for the weight of payload when mounted on said base assembly.

4. The system of claim 1, further comprising:
(a) a first table support attached to said base assembly and constructed to engage a portion of said X-ray table member when mounted on said base assembly;
(b) a second table support comprising a flat panel with a connected support wing, and said second table support being pivotally mounted on said base assembly for engagement with a portion of said X-ray table member when said X-ray table member is in a horizontal mode, and for pivotal movement to a generally horizontal position detached from said X-ray table member.

5. The system of claim 1, further comprising:
releasable clamping apparatus associated with said hinges for rendering said joints of said base assembly substantially rigid.

6. The system of claim 1, wherein:
said panels of said base assembly comprise relatively light weight honeycomb material covered by a durable composite skin.

7. The system of claim 1, further comprising:
means for adjustably leveling said base assembly.

8. The system of claim 7, wherein said leveling means comprising adjustable threaded feet.

9. The system of claim 7, further comprising:
means for indicating the attitude of said base assembly with respect to the horizontal.

10. The system of claim 1, wherein said hinges comprise compression stop plates and hinge fasteners.

11. The system of claim 4 further comprising:
(a) said support wing being hingedly coupled to said second support;
(b) second support latch apparatus releasably couplable to a portion of said support wing.

12. The system of claim 11 further comprising:
(a) an X-ray table latch apparatus for releasably holding said X-ray table member in a vertical attitude;
(b) means connecting said X-ray table latch apparatus and said second support latch apparatus for releasing said X-ray table latch apparatus in response to latching of said second support latch apparatus.

13. The system of claim 12, wherein:
said second support and said support wing are arranged such that said support wing cannot engage said second support latch apparatus unless said second support is in a substantially vertical mode.

14. The system of claim 1, further comprising:
(a) said panels of said base assembly each comprising a solid frame extending about a periphery of said panel;
(b) said hinges each comprise a pin and two body parts, each body part being connected to and adjacent one of said base assembly panels, and
(c) said hinge body portions are each integral with said frame of said adjacent base assembly panel.

15. A base assembly for supporting a deployable X-ray imaging system including an X-ray table assembly means for detachably supporting said table assembly means above said base assembly, an X-ray source, means for sensing X-ray to form an image and means for mounting said X-ray source and said X-ray sensing means on opposite sides relating to said table assembly means when mounted on said base assembly, said base assembly comprising:
(a) a plurality of substantially flat panels;
(b) hinges joining each panel to an adjacent panel along panel edges to form a segmented base;
(c) means for biasing said segmented base to exhibit a precamber when laid upon a flat surface, and to assume a substantially flat configuration when a predetermined payload is placed upon said base assembly.

16. The base assembly of claim 15, wherein said adjacent panels define mating recesses and said biasing means comprises compression stops nested in the said mating recesses.

17. The base assembly of claim 16, wherein said compression stops comprise two opposing flat plates each defining an inclined edge facing its neighbor, each of which is fastened to one of the adjacent panels.

18. The apparatus of claim 1, wherein said panels comprise a foam core and a durable outer skin.

19. The system of claim 4, wherein:
said second support comprises a foam core and glass fiber skin.

20. The system of claim 4 wherein:
said first support comprises a part having a foam core and a carbon fiber skin, and another part having a foam core and a glass fiber skin.

21. A portable X-ray imaging system including:
(a) a base assembly;
(b) an X-ray table member;
(c) apparatus for detachably mounting said table member above said base assembly;
(d) an X-ray source;
(e) means for sensing X-rays to form an image;
(f) means for mounting said X-ray source and said X-ray sensing means on opposite sides relative to said table member when mounted on said base assembly;
(g) said base assembly comprising a plurality of panels and hinges joining said panels together along edges, and
(h) means for biasing said panels to exhibit upward bowing when laid upon a flat surface before loading of other components thereon, and to assume a substantially flat configuration when a predetermined payload is placed upon said base assembly.

22. A portable X-ray image system comprising:

(a) a base assembly including a plurality of panels and hinges joining said panels together along edges, and compression stops for biasing said hinges to compensate for the weight of payload when mounted on said base assembly, said compression stops being located for interaction with said hinges for biasing said panels to exhibit upward bowing when laid upon a flat surface prior to loading, and to provide resiliency for facilitating said base assembly assuming a substantially flat configuration when a predetermined payload is placed upon said base assembly;

(b) an X-ray member;

(c) apparatus for detachably mounting a table member to said base assembly to hold said table member at a location above said base;

(d) an X-ray source;

(e) means for sensing X-rays to form an image;

(f) means for mounting said X-ray source and said X-ray sensing means on opposite sides relative to said table member and supported by said base assembly;

(g) releasable clamping apparatus associated with said hinges for rendering said joints of said base assembly substantially rigid;

(h) means for adjustably leveling said base assembly, and (i) means for indicating the attitude of said base assembly with respect to the horizontal.

23. The X-ray imaging system of claim 1, wherein said base assembly comprises:

(a) a central panel, and (b) two side panels hinged such that said side panels are both simultaneously foldable atop said center panel.

* * * * *